(12) United States Patent
Zerhusen

(10) Patent No.: US 12,405,586 B2
(45) Date of Patent: Sep. 2, 2025

(54) PERSON SUPPORT SYSTEMS AND METHODS INCLUDING A PRONING MODE

(71) Applicant: Hill-Rom Services, Inc., Batesville, IN (US)

(72) Inventor: Robert Mark Zerhusen, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 311 days.

(21) Appl. No.: 18/046,269

(22) Filed: Oct. 13, 2022

(65) Prior Publication Data

US 2023/0120653 A1    Apr. 20, 2023

Related U.S. Application Data

(60) Provisional application No. 63/270,074, filed on Oct. 21, 2021, provisional application No. 63/256,263, filed on Oct. 15, 2021.

(51) Int. Cl.
  *G05B 19/042*    (2006.01)
  *G16H 40/63*    (2018.01)

(52) U.S. Cl.
  CPC ........... *G05B 19/042* (2013.01); *G16H 40/63* (2018.01)

(58) Field of Classification Search
  USPC ...................................................... 700/279
  See application file for complete search history.

(56) References Cited

U.S. PATENT DOCUMENTS

| | | | |
|---|---|---|---|
| 7,472,440 B2 | 1/2009 | Bartlett et al. | |
| 10,176,895 B2 | 1/2019 | Vanderpohl, III | |
| 10,517,784 B2 | 12/2019 | Zerhusen et al. | |
| 10,918,546 B2 | 2/2021 | Zerhusen et al. | |
| 2007/0164871 A1 | 7/2007 | Dionne et al. | |
| 2013/0318720 A1* | 12/2013 | Connell | A61G 7/0506 5/658 |

(Continued)

FOREIGN PATENT DOCUMENTS

EP    2 783 669 B    6/2019

OTHER PUBLICATIONS

International Preliminary Report On Patentability for Appln. No. PCT/US2022/046567 mailed Apr. 25, 2024, 7 pages.

*Primary Examiner* — Ziaul Karim
*Assistant Examiner* — Joshua T Sanders
(74) *Attorney, Agent, or Firm* — Dinsmore & Shohl LLP

(57) ABSTRACT

Medical beds and methods include a processor, an input interface configured to receive commands, and a display device configured to display an output. The medical bed further includes a memory storing program instructions, the program instructions, when executed by the processor, cause the processor to place the medical bed in a restricted mode based upon satisfying a plurality of criteria. The medical bed outputs an indication of the restricted mode on the display device. The medical bed receives first and second movement commands through the input interface, wherein the movement commands are configured to move the medical bed. The medical bed moves based upon a first movement command permitted by the restricted mode. The medical bed maintains a current state of the medical bed upon receipt of a second movement command blocked by the restricted mode, wherein the second movement command differs from the first movement command.

20 Claims, 16 Drawing Sheets

(56) References Cited

U.S. PATENT DOCUMENTS

| | | |
|---|---|---|
| 2019/0262204 A1 | 8/2019 | Hertz et al. |
| 2020/0178702 A1* | 6/2020 | Shiino .................. A47C 21/003 |
| 2020/0323354 A1 | 10/2020 | Newkirk et al. |
| 2020/0405554 A1 | 12/2020 | Kuperberg |
| 2021/0045950 A1* | 2/2021 | Connell ................. A61G 7/015 |
| 2021/0353179 A1* | 11/2021 | Sukumaran .......... A61G 7/0528 |
| 2022/0122724 A1* | 4/2022 | Durlach ................. A61B 5/002 |

* cited by examiner

PERSON SUPPORT SYSTEMS AND METHODS INCLUDING A PRONING MODE

The present application claims the priority benefit of U.S. Provisional Application No. 63/256,263, entitled "PERSON SUPPORT SYSTEMS AND METHODS INCLUDING A PRONING MODE" and filed Oct. 15, 2021 and claims the priority benefit of U.S. Provisional Application No. 63/270,074, entitled "PERSON SUPPORT SYSTEMS AND METHODS INCLUDING A PRONING MODE" and filed Oct. 21, 2021, the entire contents of both are incorporated herein.

BACKGROUND

Field

The present specification generally relates to person support apparatuses and, more specifically, to person support apparatuses that prohibit specific types of movement when in a proning mode.

Technical Background

People receive care in support apparatuses such as beds for a variety of reasons. For some types of care, a person is placed into a prone position, in which they are face-down. While in the prone position, a person may be more susceptible to injury if they are manipulated in improper ways. For example, raising a person's legs too high while in the prone position may be uncomfortable and/or cause injury.

On a traditional bed that merely has a mattress to lay upon, a person does not face this type of risk when in the prone position. However, a person in a prone position on more specialized medical equipment, such as medical beds, may face risk of pain and/or injury. For example, articulating a medical bed too dramatically can accidentally contort the person's back and spine. Thus, safeguarding a person in a medical bed while in a prone position can protect them, irrespective of the reason the person is placed into the prone position.

SUMMARY

In one aspect, a medical bed may include a processor, an input interface configured to receive commands, a display device configured to display an interface, and a memory storing program instructions. The program instructions, when executed by the processor, cause the processor to place the medical bed in a restricted mode based upon satisfying a plurality of criteria. The program instructions also cause the process to output an indication of the restricted mode on the display device. The program instructions further cause the processor to receive first and second movement (e.g. articulation) commands through the input interface, wherein the movement commands are configured to move (e.g. articulate) the medical bed. The program instructions further cause the processor to move the medical bed based upon a first movement command permitted by the restricted mode. The program instructions further cause the processor to maintain a current state of the medical bed upon receipt of a second movement command blocked by the restricted mode, wherein the second movement command differs from the first movement command.

In such an aspect, the criteria are the medical bed being level, the medical bed being configured to straighten legs of a user in the medical bed, the medical bed being configured to lower a back of the user in the medical bed, and an out-of-bed exit mode being on. In another aspect, the restricted mode is contingent upon prior receipt of input confirming a request to enter the restricted mode. In yet another aspect, the restricted mode is based upon prior input confirming entry into the restricted mode. In a further aspect, exit from the restricted mode is contingent upon receipt of input confirming exit from the restricted mode. In an additional aspect, a head support device configured to support a head of user in a prone position. In yet another aspect, a sensor detects that the head support device is present such that an additional criteria comprises the head support device being level with a support surface of the medical bed. In an additional aspect, a weight measurement of a user is prevented upon detection of the head support device. In another aspect, the method further includes detecting, via a sensor, that the head support device is present, wherein the criteria further include a criterion that the head support device is level with a support surface of the medical bed. In yet another aspect, the memory stores data regarding proning mode historical data of the medical bed. In a further aspect, the proning mode historical data is stored remotely. In an additional aspect, the proning mode historical data is stored in an electronic medical record. In yet another aspect, the second movement command comprises position bed mode, exit bed mode, back movement, leg movement, Trendelenburg position, reverse Trendelenburg position, chair position, boost, or bed up/down. In another aspect, the second command being blocked by the restricted mode results in a visual or audio notification. In a further aspect, a bed adjustment input button is configured to move the medical bed to satisfy all the criteria to enter the restricted mode.

In yet another aspect, a method for conditionally-restricted medical bed operation may include placing the medical bed in a restricted mode based upon satisfying a plurality of criteria. The method may further include outputting an indication of the restricted mode on a display device of the medical bed. The method may further include receiving first and second movement commands through an input interface of the medical bed, wherein the movement commands are configured to move the medical bed. The method may further include articulating the medical bed based upon a first movement command permitted by the restricted mode. The method may further include maintaining a current state of the medical bed upon receipt of a second movement command blocked by the restricted mode, wherein the second movement command differs from the first movement command.

In such still a further aspect, according to some aspects, the criteria are the medical bed being level, the medical bed being configured to straighten legs of a user in the medical bed, the medical bed being configured to lower a back of the user in the medical bed, and an out-of-bed exit mode being on. In another aspect, the restricted mode is contingent upon prior receipt of input confirming a request to enter the restricted mode. In yet another aspect, the restricted mode is based upon prior input confirming entry into the restricted mode. In a further aspect, exit from the restricted mode is contingent upon receipt of input confirming exit from the restricted mode. In an additional aspect, the method includes using a head support device to support the head of a subject in a prone position. In yet another aspect, the method further includes detecting, via a sensor, that the head support device is present, wherein the criteria further include a criterion that the head support device is level with a support surface of the medical bed. In yet a further aspect, the method includes preventing a weight measurement of the subject upon detection of the head support device. In an additional aspect, the method further includes indicating a current proning mode status to a remote device via a communication component. In yet another aspect, the method further includes storing data regarding proning mode historical data of the medical bed. In a further aspect, the method further includes storing the proning mode historical data remotely. In an additional aspect, the method include storing the proning mode historical data in an electronic medical record. In yet another aspect, the second movement command comprises position bed mode, exit bed mode, back movement, leg movement, Trendelenburg position, reverse Trendelenburg position, chair position, boost, or bed up/down. In another aspect, the second command being blocked by the restricted mode results in a visual or audio notification. In a further aspect, the method includes articulating the medical bed to satisfy all the criteria to enter the restricted mode based upon input received at a bed adjustment input button. In a further aspect, a system comprises a processor and a non-transitory, computer readable storage medium communicatively coupled to the processor, such that the non-transitory, computer readable storage medium includes one or more programming instructions stored thereon that, when executed by the processor, cause the processor to carry out the method according to the preceding claims. In another aspect, a software program stored on a non-transitory, computer readable storage medium includes one or more programming instructions that, when executed by a processor, cause the processor to carry out the method according to the preceding claims.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1A:
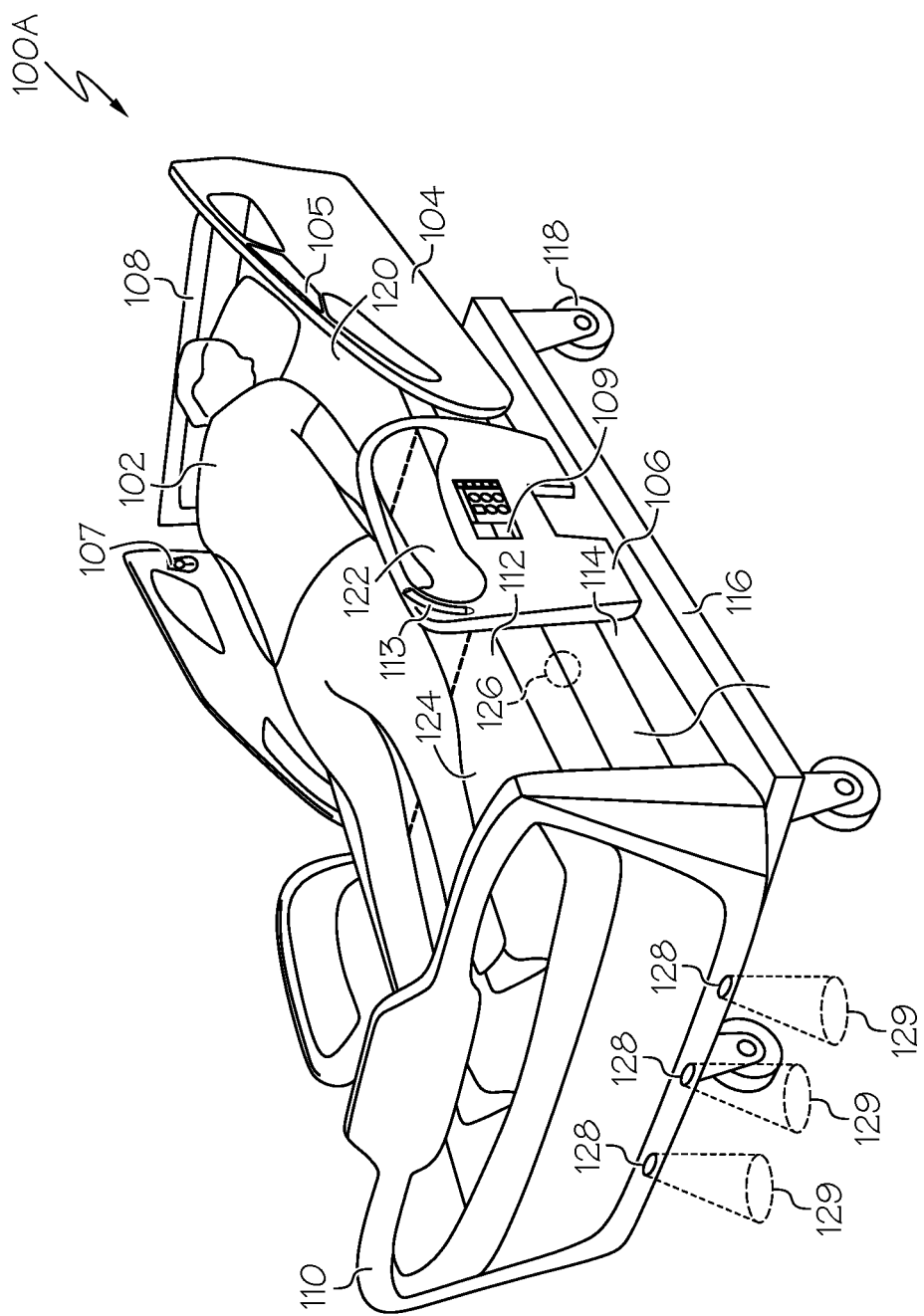
FIG. 1A depicts an embodiment of a medical bed containing a person in a prone position, according to one or more embodiments shown and described herein.

Reference will now be made in detail to embodiments for a medical bed to utilize a proning mode, in which a medical bed supports a subject laying on their abdomen, and in which only certain movement (e.g., articulation) commands to modify the medical bed are allowed to be executed during proning mode in order to not disturb the subject's prone position, examples of which are illustrated in the accompanying drawings. Whenever possible, the same reference numerals will be used throughout the drawings to refer to the same or like parts.

FIG. 1A depicts an embodiment of a medical bed 100A containing a person (referred to hereinafter as a subject 102) in a prone position. Although the term "medical bed" is utilized herein, any suitable type of support system may be utilized to support a subject 102, such as by way of non-limiting example gatch beds, full electric beds, semi-electric beds, low air loss beds, circo-electric beds, clinitron beds, and/or any other suitable support system. The medical bed 100A may feature, on the inside surface of the upper side rails 104 near the subject's head, one or more subject control panels 107 to provide the subject 102 with control over the medical bed 100A. Specific examples of subject control panels 107 are discussed with respect to FIGS. 1C and 2C. The upper side rails 104 may also feature a user control panel 105. Users may include medical personnel and/or anyone capable of operating a subject control panel 107. Specific examples of user control panels 105 are discussed with respect to FIGS. 1B and 2B. User control panels 105 and/or subject control panels 107 may utilize any suitable type of configuration (membrane switch panel, button panel, flat control panel, console type control panel, breakfront panel, touch screen, and the like). A graphical user interface 109 may be provided on the lower side rail 106. An example of a graphical user interface 109 is provided in FIG. 4 and may be implemented using a touch screen and the like. The user control panel 105, subject control panel 107, and/or graphical user interface 109 may be utilized to modify operations of the medical bed 100A. Other portions of the medical bed 100A may include a head rail 108 and/or a foot rail 110, which may be moveable as described in more detail with respect to 414 in FIG. 4.

The subject 102 may lie upon a support surface 112 (also known as a top layer and/or mattress, used interchangeably herein), which may utilize any suitable type of material capable of supporting a subject 102, such as foam and the like. The support surface 112 has different sections that can move separately, such as a head portion 120, a middle portion 122, and a foot portion 124, as separated by the dashed lines running under the subject 102. This can in turn lower/elevate different portions of the medical bed 100A, such as the head portion 120 of the medical bed 100A to move the head/back of the subject 102, the middle portion 122 (to move the subject's thighs), and the foot portion 124 of the medical bed 100A to move the subject's feet. An upper frame 115 may reside beneath the support surface 112, which, along with an intermediate frame 114 further beneath the upper frame 115, the lower frame 116, and/or the intermediate frame 114, may move (e.g., articulate) to raise/lower or otherwise move various portions of the support surface. One or more actuators may be located at the foot edge/end of the medical bed 100A beneath the support surface 112, such as above, below, or within any of the upper frame 115, the intermediate frame 114, and/or the lower frame 116, in order to raise/lower the feet of the subject 102 without necessarily affecting other portions of the subject 102 such as their torso, arms, or head, such that their feet may be lowered with their knees becoming bent but remaining substantially level with their head. One or more actuators may also be located beneath the at the border of where the foot portion 124 meets the middle portion 122 beneath the support surface 112, such as above, below, or within any of the upper frame 115, the intermediate frame 114, and/or the lower frame 116, in order to raise/lower the knees of the subject 102 without necessarily affecting other portions of the subject 102, such as having the subject 102 lying on their back with their knees bent, such that their feet may remain substantially level with their head. One or more actuators may be located at the head edge/end of the medical bed 100A beneath the support surface 112, such as above, below, or within any of the upper frame 115, the intermediate frame 114, and/or the lower frame 116, in order to raise/lower the head/torso of the subject 102 without necessarily affecting lower portions of the subject 102 such as their legs, such as putting the subject 102 in a seated position. One or more actuators may dispersed to provide support under the entirety of the support surface 112 (i.e., above/below/within the upper frame 115, the lower frame 116, and/or the intermediate frame 114). Having actuators widely dispersed below the intermediate frame 114, for example, can allow the uniform raising/lowering of the entirety of the support surface 112 or to allow a uniform angle such as the 16° Trendelenburg position discussed herein with respect to control 150 in FIG. 1B (positioning the subject via the actuators acting upon the support surface 112 such that their head is declined below their feet). One or more weight sensors 126 (strain gauge, capacitance, hydraulic, pneumatic, and the like) may be utilized in some embodiments and are depicted as residing directly underneath the support surface 214 but may be located in any suitable portion of the medical bed 100A in order to weigh the subject 102 and/or detect their movement(s). Wheels 118 may be attached to the lower frame 116 and/or any other suitable portion(s) to facilitate mobility/transport of the medical bed 100A. Other embodiments may utilize different components and/or configurations.

A proning mode color indicator 113 in the exemplary form of a light emitting diode (LED) or other suitable light source may be used indicate that the function represented by a button is not presently available, such as turning a particular color to indicate that a requested button being pressed is not available. Status lights 128 are depicted as being located along the bottom of the foot rail 110, although status lights may be located on any suitable location on the medical bed 100A. Any suitable type of light source (light emitting diode, compact fluorescent light bulbs, lasers, and the like) may be utilized to make corresponding status light projections 129, which may be projected onto any surface such as the floor as depicted in this embodiment. The status light may project, by way of non-limiting example, any suitable information, such as status information regarding the current positioning and/or operating condition of the medical bed 100A, and/or alerts such as the out-of-bed exit alert and/or the non-selectable icons discussed herein.

Figure 1B:
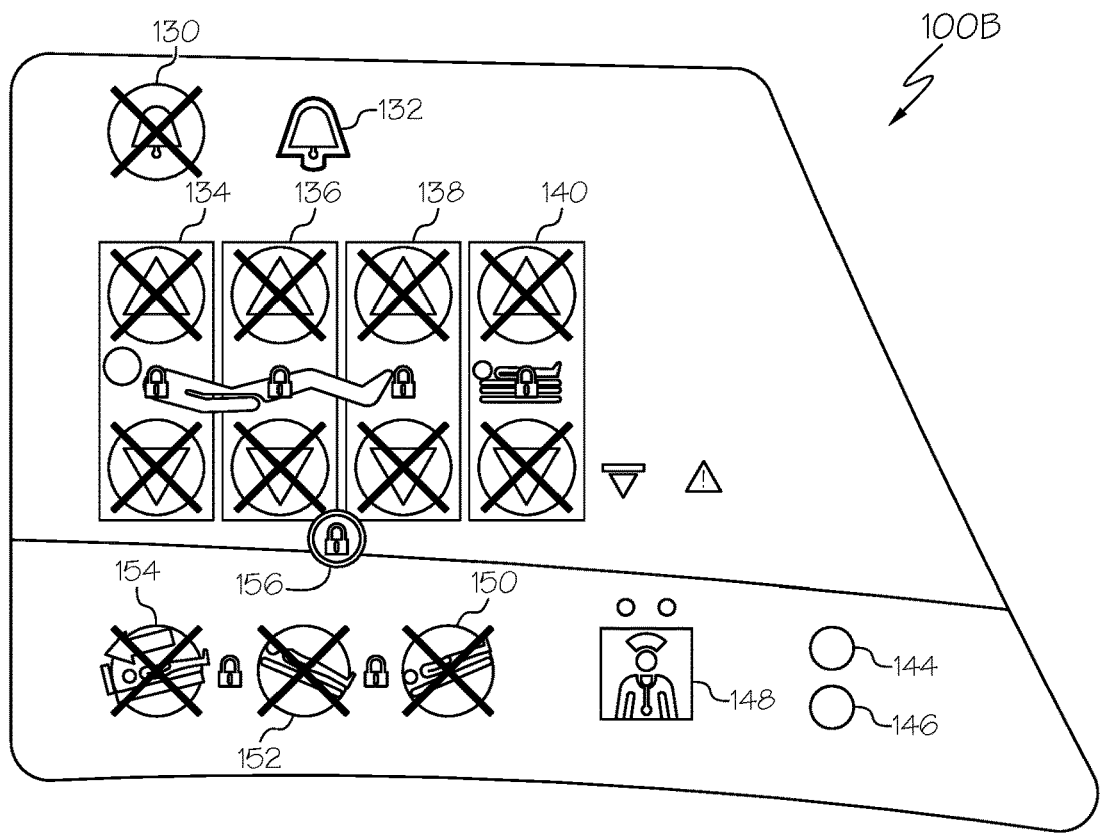
FIG. 1B depicts an exemplary user control panel that may be utilized by medical personnel to move the medical bed depicted in FIG. 1A with control options marked as restricted merely for illustrative purposes, according to one or more embodiments shown and described herein.

FIG. 1B depicts an exemplary user control panel 100B that may be utilized by users (such as medical personnel) to move the medical bed depicted in FIG. 1A. However, when the medical bed is in proning mode (i.e., the head portion 120 supporting the head in a substantially horizontal position, the middle portion 122 supporting torso, arms, and the top of the legs in a substantially horizontal position, and the foot portion 124 supporting the bottom of the legs in a substantially horizontal position, which taken together form a continuously substantially horizontal support surface 112), various functionalities may not be available to the extent that they may disrupt the substantially horizontal positioning of the continuously substantially horizontal support surface 112. By way of non-limiting examples, unavailable functionalities may include alert silence control 130 that silences various alerts (which may not be available because important alerts pertinent to prone position may need to be heard/seen), head up/down controls 134 (head portion 120 swings upward/downward with respect to its border with the middle portion 122), knee up/down controls 136 (the border of the foot portion 124 and the middle portion 226 raises up to form a sharper angle or lowers to reduce the angle), foot up/down controls 138 (foot portion 124 swings upward/downward with respect to its border with the middle portion 122), bed up/down controls 140 (raising/lowering at least the support surface 112 by actuators located above/below/between any of the intermediate frame 114, upper frame 115, and/or lower frame 116), Trendelenburg control 150 (positioning the subject such that their head is declined below their feet at an angle of roughly 16° or any suitable angle), reverse Trendelenburg control 152 (positioning the subject such that their feet are declined below their head at an angle of roughly 16° or any suitable angle), and boost position control 154 (maximum mattress inflate, flattening the medical bed 100A and placing it in a 7° reverse Trendelenburg position in which the head is lower than the feet). One or more controls may have a lockout indicator 156 that may be in the form of a graphic (such as a lock) illuminated by light if a button (wherein any physical button may be backlit with any suitable type of internal light source) or displayed on a screen as a graphical icon. Restricted (or locked-out, used interchangeably herein) button are shown with an 'X' merely to make them easily discernible within the figures herein.

The alert silence control 130 may include an LED and may be used to silence alerts, which is not permitted in this embodiment when proning mode is in use. The head up/down controls 134, knee up/down controls 136, and foot up/down controls 138 may be restricted in proning mode to ensure that the subject's body remains in a proper horizontal prone position during proning mode. Movement commands, such as the bed up/down controls 140, may be restricted so that they are not executed if pressed or otherwise selected during proning mode to ensure that the subject remains properly accessible at the right height, and to ensure proper head and neck support when a head support is utilized (see FIGS. 3A and 3B). As discussed further herein, feedback indicating that an movement command is restricted or otherwise unavailable may be indicated to a user or subject 102 by a visual alert (change in color or brightness of icons or a light such as the proning mode color indicator 1206 in FIG. 12 located separately on the medical bed 100A) and/or an audio alert (beep, tone, voice) indicating as such. Trendelenburg control 150 (i.e., head position lower than feet) and reverse Trendelenburg control 152 (i.e., head positioned higher than feet) may be disabled to ensure a proper horizontal prone position for the subject. The boost position control 154 may be disabled to prevent lowering of the subject's head while leveling their knees, which would deviate from the prone position.

Controls that remain active in proning mode are movement commands that remain executable in proning mode, as opposed to restricted that are unavailable during proning mode. Controls that remain active in proning mode may include, by way of non-limiting example, the bed exit alert ON indicator 132 to indicate that the subject is trying to leave the medical bed, set brake indicator 144, battery charging indicator 146, and the nurse call control 148, none of which interfere with the subject getting into or remaining in the prone position in this embodiment.

In this embodiment, proning mode may include several criteria to be met before proning mode can be engaged, although some criteria may be optional in some embodiments. A first criterion is whether the medical bed 100A is level. This may mean, for example, that the intermediate frame 114 is substantially or exactly horizontal, rather than at a tilt. The change in the angle of the medical bed 100A, with respect to the orientation of the intermediate frame 114 in this embodiment (any other portion/component of the medical bed 100A may be utilized in other embodiments) may be communicated by actuators located in the medical bed 100A in communication with, for example, a processor 1602 associated with the medical bed 100A as depicted FIG. 16. A second criterion is whether the medical bed 100A has straightened the legs of the subject 102. This may mean, for example, that the foot portion 124 is substantially level with the middle portion 122, such that the legs of the subject 102 lie flat with the rest of their body. The change in the relative angle of the medical bed 100A between the foot portion 124 and the middle portion 122 may be communicated by actuators located in the medical bed 100A in communication with, for example, a processor 1602 associated with the medical bed 100A as depicted FIG. 16.

A third criterion is whether the medical bed 100A has lowered the back of the subject 102. This may mean, for example, that the head portion 120 is substantially level with the middle portion 122, such that the torso of the subject 102 lies flat with the rest of their body. The change in the relative angle of the medical bed 100A between the head portion 120 and the middle portion 122 may be communicated by actuators located in the medical bed 100A in communication with, for example, a processor 1602 associated with the medical bed 100A as depicted FIG. 16. A fourth criterion is whether the medical bed 100A has an out-of-bed exit mode engaged. Having the out-of-bed exit mode may mean, for example, that the medical bed 100A provides an alert if the subject 102 tries to leave the medical bed 100A, visual alert (change in color or brightness of icons or a light such as the proning mode color indicator 1206 in FIG. 12 located separately on the medical bed 100A) and/or an audio alert (beep, tone, voice) indicating as such. This may be detected, for example, by the weight sensor(s) 126 in communication with, for example, a processor 1602 associated with the medical bed 100A as depicted FIG. 16.

Figure 1C:
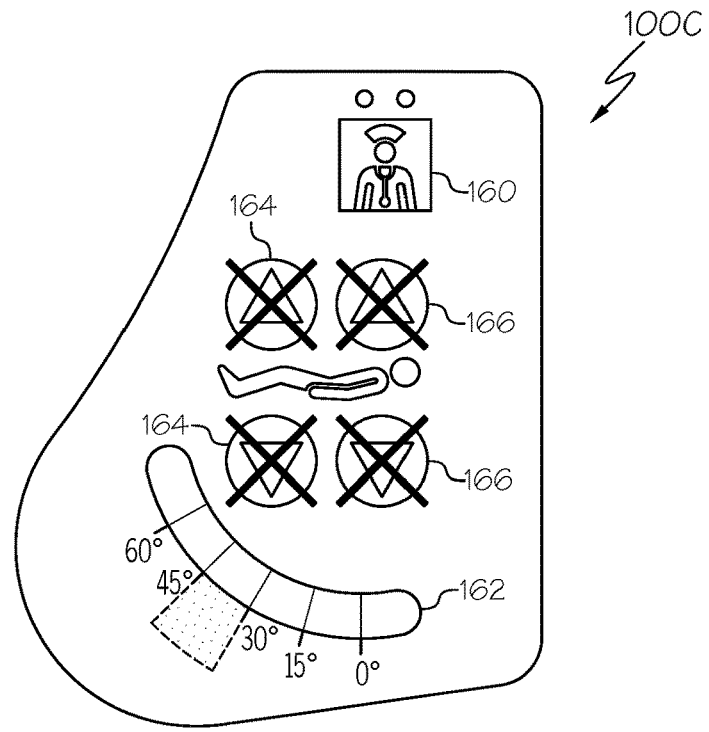
FIG. 1C depicts an exemplary subject control panel that may be utilized to move the medical bed depicted in FIG. 1A by the person lying in it with control options marked as restricted merely for illustrative purposes, according to one or more embodiments shown and described herein.

FIG. 1C depicts an exemplary subject control panel 100C that may be utilized to move the medical bed depicted in FIG. 1A by the subject lying in it. The subject control panel may have fewer controls than the user control panel, as it may be designed to be used by the subject lying in the medical bed, and may be more simplified with fewer commands available. Similar to the user control panel 100B depicted in the FIG. 1B, knee up/down controls 164 and/or head up/down controls 166 may be restricted during proning mode to protect the subject, while the nurse call control 160 with LED indicators remains available. In some embodiments, the subject control panel 100C may be in the form of a remote control device, which, for example, can be handheld by the subject. The angular indicator 162 does not receive input in this embodiment, as it only outputs an angular value of the subject, and remains active during proning mode.

Figure 2A:
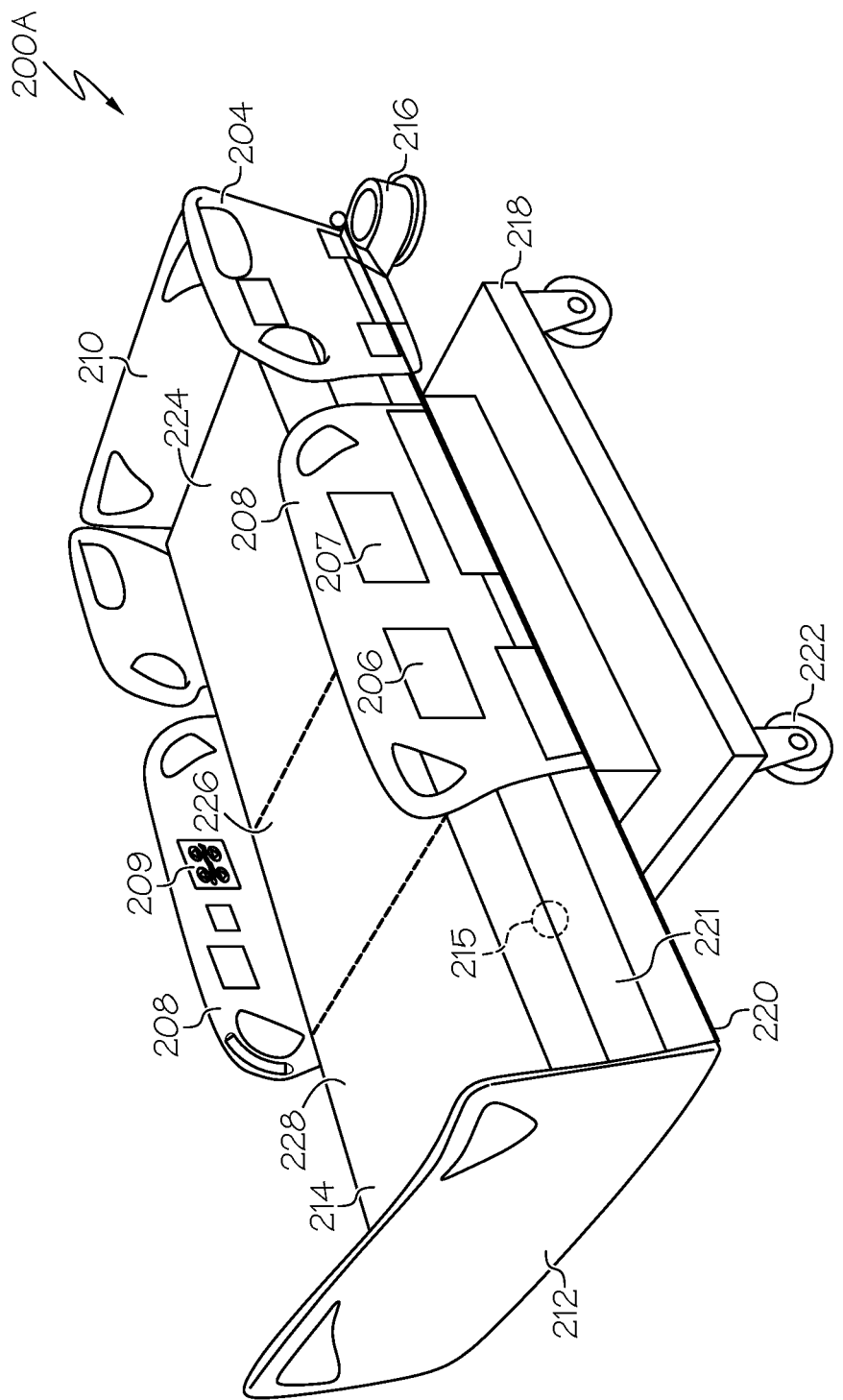
FIG. 2A depicts another exemplary embodiment of a medical bed, according to one or more embodiments shown and described herein.

FIG. 2A depicts another embodiment of a medical bed 200A, which may feature on the inside surface of the side portions 208 one or more subject control panels 209 to provide the subject with control over the medical bed 200A. A graphical user interface 206 may also be provided on the side portions 208. The user control panel 207, subject control panel 209, and/or graphical user interface 206 may be utilized to modify operations of the medical bed 200A. The upper side portions 204 may also feature a user control panel 207. Other portions of the medical bed 200A may include a head rail 210 and/or a foot rail 212.

The subject may lay upon a support surface 214, which can move, as indicated by the dashed lines running across the support surface 214, to lower/elevate different portions of the medical bed 200A, such as a head portion 224 of the medical bed 200A to move the head/back of the subject, a middle portion 226 (to move the subject's thighs), and a foot portion 228 of the medical bed 200A to move the subject's feet. An intermediate frame 221 may reside beneath the support surface 214, which, along with a lower frame 220 beneath the intermediate frame 221, may move to raise/lower or otherwise move various portions of the support surface 214. One or more actuators may be located at the foot edge/end of the medical bed 200A beneath the support surface 214, such as above, below, or within any of the intermediate frame 221, the lower frame 220, and/or the base 218, in order to raise/lower the feet of the subject. One or more actuators may also be located beneath the at the border of where the foot portion 228 meets the middle portion 122 beneath the support surface 214, such as above, below, or within any of the intermediate frame 221, the lower frame 220, and/or the base 218, in order to raise/lower the knees of the subject without necessarily affecting other portions of the subject. One or more actuators may be located at the head edge/end of the medical bed 200A beneath the support surface 214, such as above, below, or within any of intermediate frame 221, the lower frame 220, and/or the base 218, in order to raise/lower the head/torso of the subject without necessarily affecting lower portions of the subject. One or more actuators may dispersed to provide support under the entirety of the support surface 214 (i.e., above/below/within the intermediate frame 221, the lower frame 220, and/or the base 218). Having actuators widely dispersed below the intermediate frame 221, for example, can allow the uniform raising/lowering of the entirety of the support surface 214 or to allow a uniform angle.

One or more receiving portions 216, which may be attached to the lower frame 220 or any other suitable portion of the medical bed 200A, may be utilized to secure the head support (discussed with respect to FIGS. 3A and 3B) and/or any other type of attachment. One or more weight sensors 215 (strain gauge, capacitance, hydraulic, pneumatic, and the like) are depicted as residing directly underneath the support surface 214 but may be located in any suitable portion of the medical bed 200A to weigh the subject and/or detect their movement. Wheels 222 may be attached to the base 218 or any other suitable portion(s) of the medical bed 200A to facilitate mobility/transport of the medical bed 200A. Other embodiments may utilize different components and/or configurations.

Figure 2B:
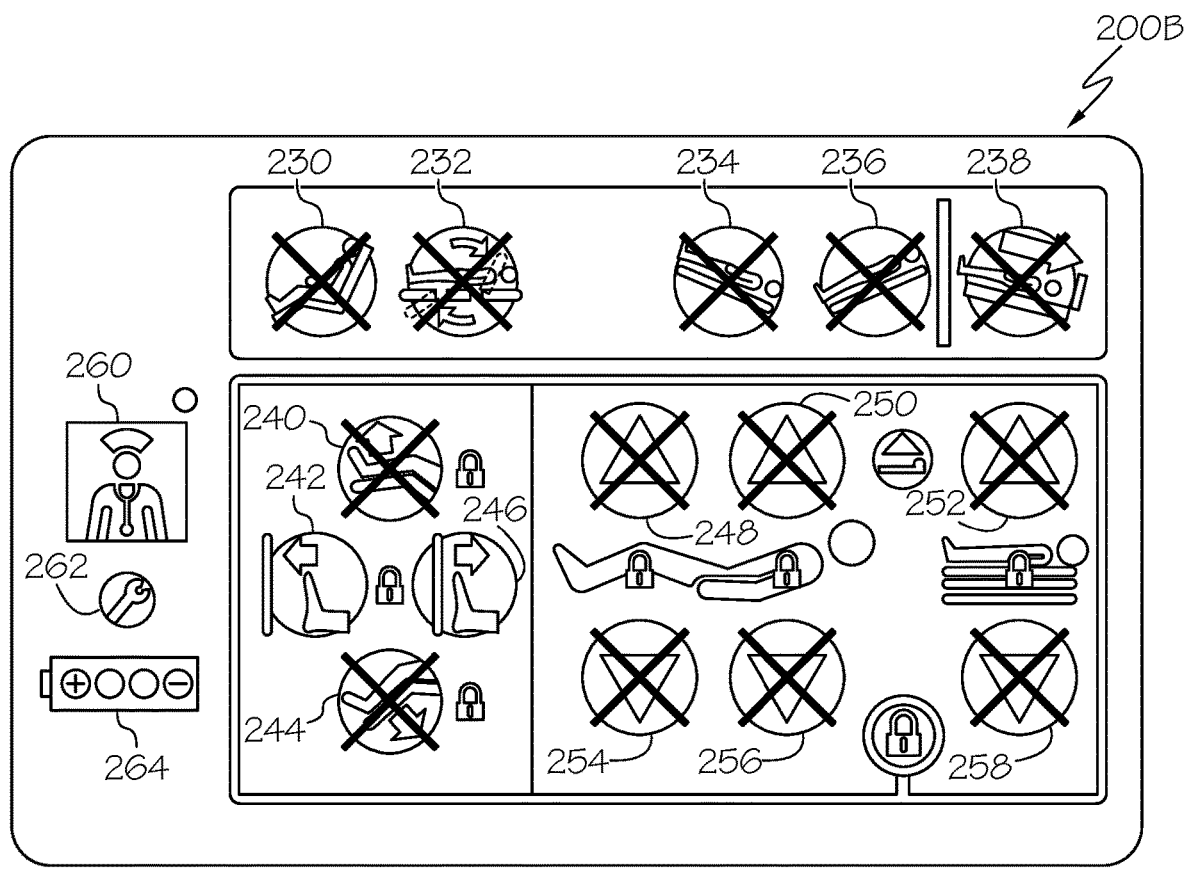
FIG. 2B depicts an exemplary user control panel that may be utilized by medical personnel to move the medical bed depicted in FIG. 2A with control options marked as restricted merely for illustrative purposes, according to one or more embodiments shown and described herein.

FIG. 2B depicts an exemplary control panel 200B that may be utilized by users to move the medical bed depicted in FIG. 2A with control options (also referred to herein as movement commands), some of which may be marked as restricted during proning mode. Buttons restricted in this embodiment during proning mode may include, by way of non-limiting example, chair control 230 and flattening control 232 as described in further detail herein. Other restricted buttons include Trendelenburg control 234 (described with respect to 150 FIG. 1B), reverse Trendelenburg control 236 (described with respect to 152 FIG. 1B), boost position control 238 (described with respect to 238 FIG. 1B), foot raising control 240 (described with respect to 138 FIG. 1B), foot lowering control 244 (described with respect to 138 FIG. 1B), knee raising control 248 (described with respect to 136 FIG. 1B), head raising control 250 (described with respect to 134 FIG. 1B), bed raising control 252 (described with respect to 140 FIG. 1B), knee lowering control 254 (described with respect to 136 FIG. 1B), head lowering control 256 (described with respect to 134 FIG. 1B), bed lowering control 258 (described with respect to 140 FIG. 1B). For example, the chair control 230 movement command is not suitable for a prone subject because this movement command raises the head portion 224 and lowers the foot portion 228 to create a seated position, which could be uncomfortable and/or disruptive to maintaining prone positioning in which the head, torso, arms, and legs are substantially aligned along the support surface 214. Similarly, changing the rotational aspect of the subject with the flattening control 232 is not suitable for a prone subject because this movement command modifies the angle of the head portion 224 and foot portion 228 relative to the middle portion 226, which could be uncomfortable and/or disruptive to maintaining prone positioning in which the head, torso, arms, and legs are substantially aligned along the support surface 214. By contrast, the bed lengthening control 242 and bed shortening control 246 (i.e., modifying the position of the footboard relative to the subject's feet), nurse call control 260 (described with respect to 148 FIG. 1B) with an LED indicator, service required indicator 262 that can be utilized in some embodiments to request service/maintenance of the medical bed, and battery charging indicator 264 remain fully operational during proning mode. For example, the subject can utilize the nurse call control 260 regardless of whether or not the medical bed is in proning mode.

Figure 2C:
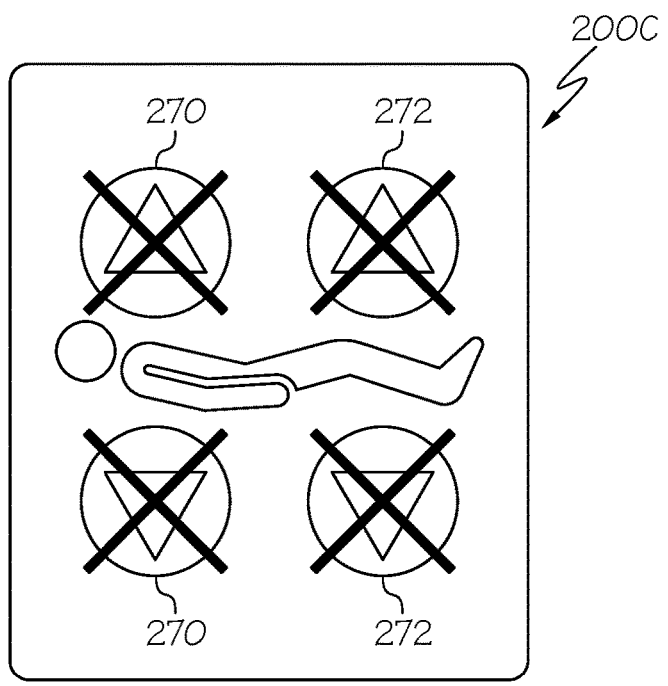
FIG. 2C depicts an exemplary subject control panel that may be utilized to move the medical bed depicted in FIG. 2A by the person lying in it with control options marked as restricted merely for illustrative purposes, according to one or more embodiments shown and described herein.

FIG. 2C depicts an exemplary subject control panel 200C that may be utilized to move the medical bed depicted in FIG. 2A by the subject lying in it. Similar to the subject control panel in the embodiment depicted in FIG. 1C, the head up/down controls 270 and the knee up/down controls 272 are movement commands that may be restricted during proning mode to ensure that the subject enters and remains in a proper prone position.

Figure 3A:
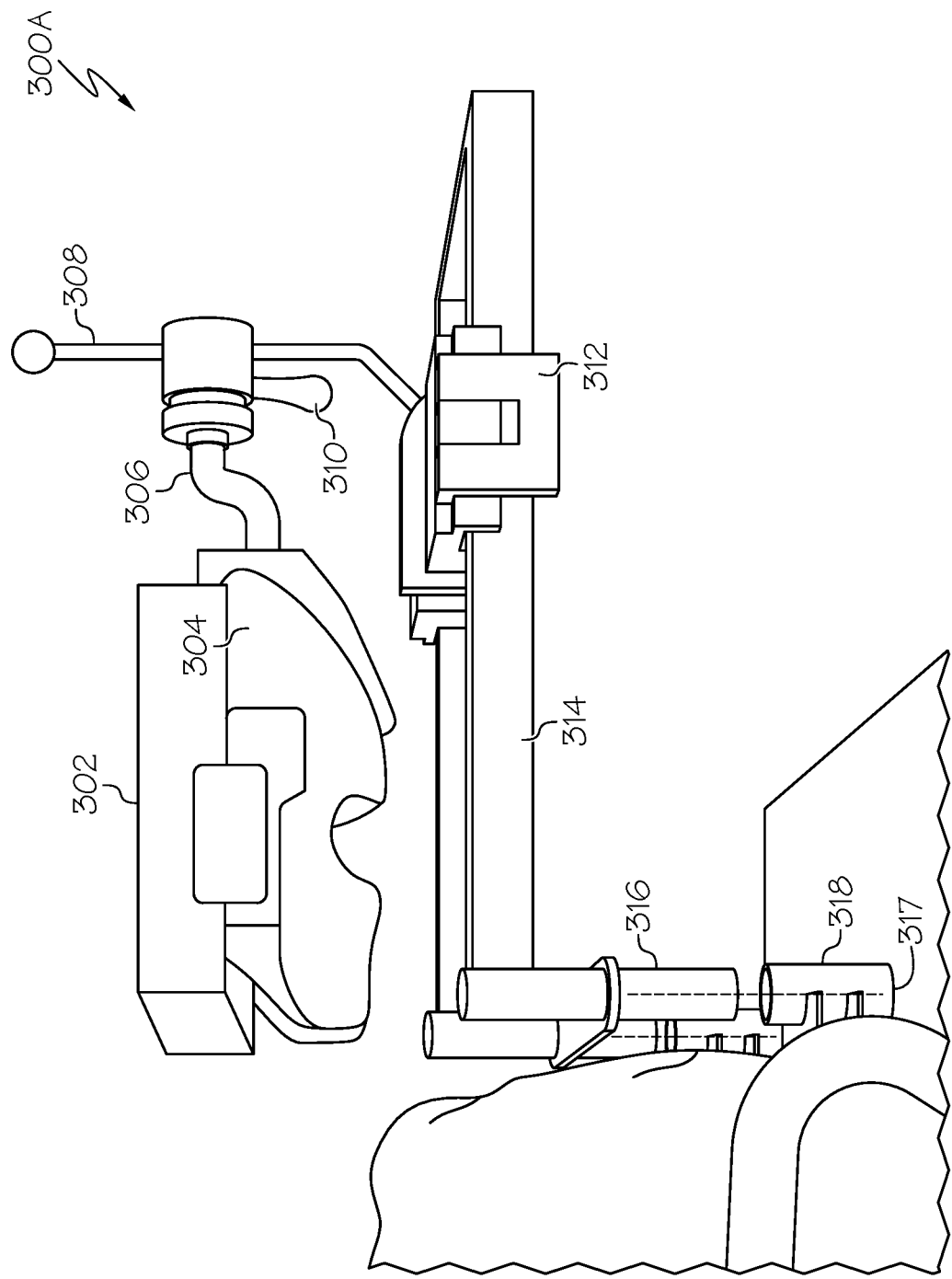
FIG. 3A depicts a head support attachment unit that may be utilized with the medical bed embodiments depicted herein to support the head of person in a prone position, according to one or more embodiments shown and described herein.

FIG. 3A depicts a head support attachment unit that may be utilized with the medical bed embodiments depicted herein to support the head of a prone subject. In this embodiment, the head support 300A is optional, but in some embodiments may be required and/or be permanently attached/affixed to a medical bed. The head support 300A in this embodiment includes a pad 302 which may include openings for the subject's eyes, nose, mouth, etc., and may reside atop a head section frame 304. A legged support arm 306 may connect the head section frame 304 to a handled portion 310 that adjustably resides on a post 308. The handled portion 310 can be loosened by rotating the handle to increase/decrease the tightness of the handled portion gripping the post 308 that runs vertically through the handled portion 310. In this way, the handled portion 310 can be used to adjust its vertical position on the post 308, and thus adjust the height of the head support 300A relative to the medical bed. This height adjustment may be used to ensure a proper prone position for a subject lying prone on the medical bed. The post 308 may be secured to the head support 314 by a clamp 312 or any other suitable mechanism (fasteners and the like).

Some embodiments of the medical bed, such as the receiving portion 216 of the medical bed embodiment depicted in FIG. 2A may correspond to sockets 318 protruding from the head rail 210 of the medical bed in FIG. 3A. One or more socket sensors 317 (weight sensor, motion sensor, pressure and the like) may reside in one or more of the sockets 318 and may be adhesively affixed to the interior of a socket 318 or may remain in place due to a tight fit or other friction. The socket sensors 317 may be utilized in some embodiments to detect the presence of one or both attachment members 316 of the head support 300A. The attachment members 316 may extend downward from the head support 314 to slide into the sockets 318 of the medical bed, such that the circumference of the openings of the sockets 318 may slightly exceed the circumference of the attachment members 316 to ensure a secure fit. By detecting the attachment of the head support 300A to the medical bed, the operation of the medical bed may be modified accordingly. For example, as further discussed with respect to FIG. 11, using the head support (i.e., out-of-bed proning) may result in the scale function (i.e., weighing) being disabled, since the subject's head is not being weighed by the medical bed, which would thus give an inaccurate weight. By contrast, having the entirety of the subject on the support surface within the medical bed (i.e., in-bed proning) would yield an accurate weight for the subject by comparison, and the scale option thus remains enabled during in-bed proning.

Figure 3B:
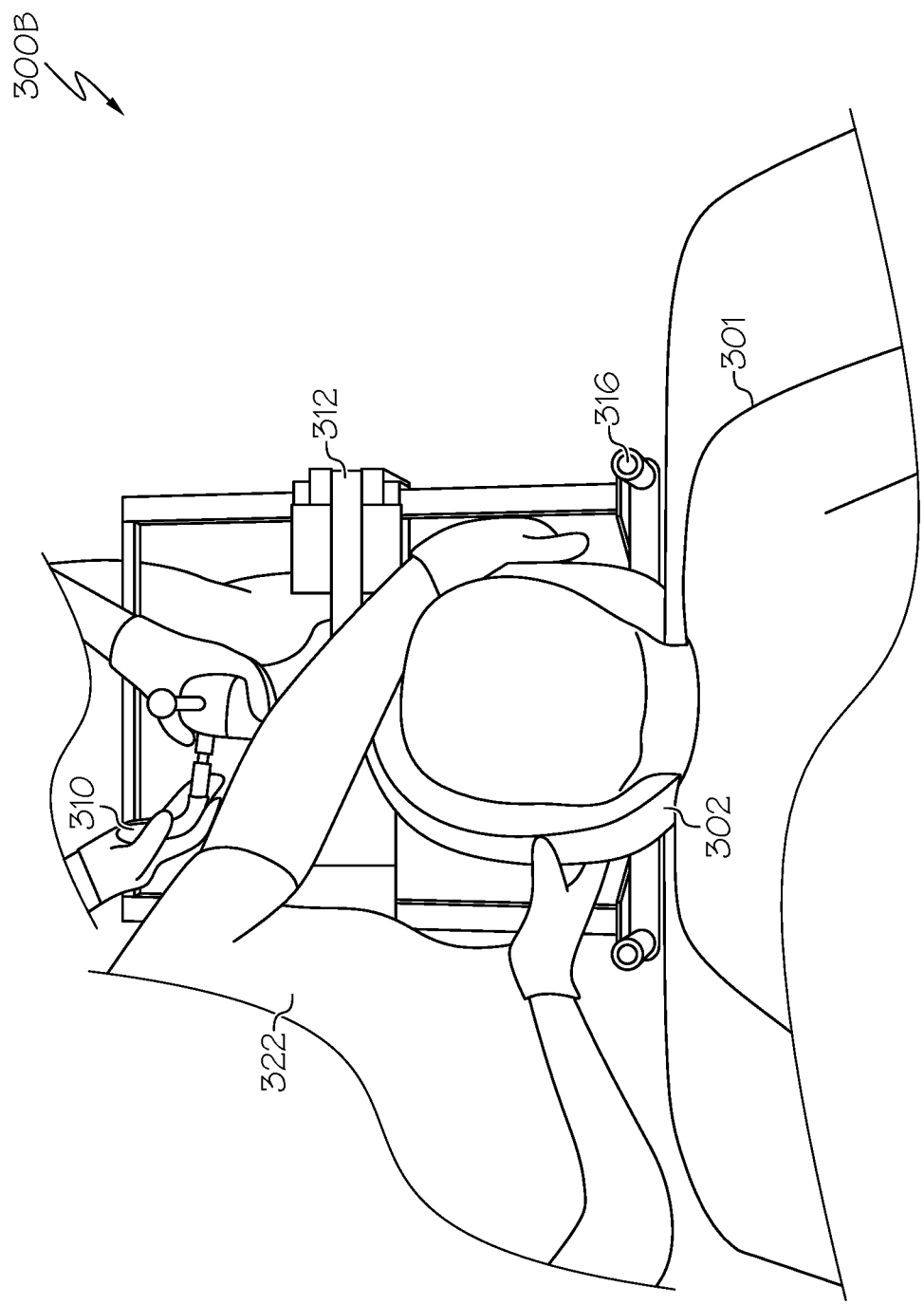
FIG. 3B depicts a person whose head is being placed in the head support attachment unit depicted in FIG. 3A by medical personnel, according to one or more embodiments shown and described herein.

FIG. 3B provides an overhead view of a subject 301 in the prone position (e.g., face down) whose head is being placed in the head support attachment unit depicted in FIG. 3A by medical personnel such as a user 322. As part of the proning of the subject 301, in which the subject 301 lies face down with their head, arms, torso, and legs substantially aligned along the same horizontal axis (i.e., the support surface 214), the handled portion 310 of the head support 300B may be adjusted to give the subject proper support with their face pressed down against the pad 302.

Figure 4:
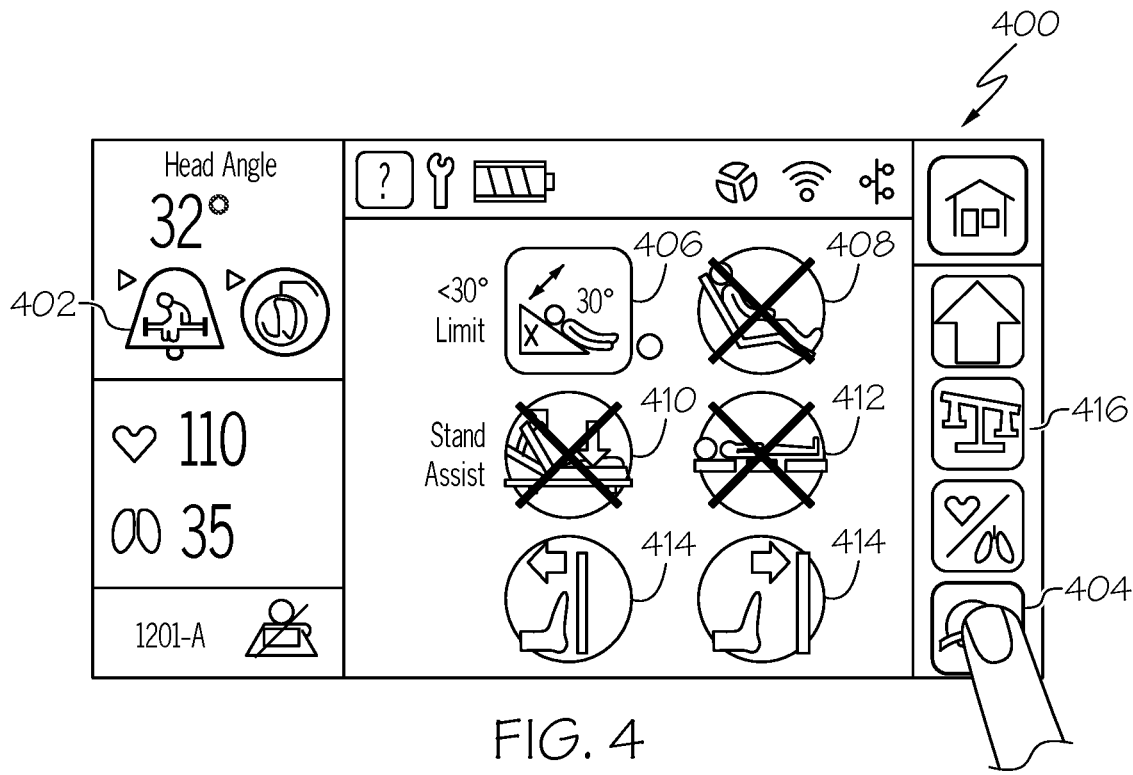
FIG. 4 depicts an exemplary graphical user interface that may be utilized by medical personnel to move a medical bed subject to control options marked as restricted merely for illustrative purposes, according to one or more embodiments shown and described herein.

FIG. 4 depicts an exemplary graphical user interface that may be utilized by medical personnel to move a medical bed. Movement commands that cannot be executed in proning mode may be represented by the non-selectable icons as shown with an 'X' or any suitable graphical indicator of non-selectability (e.g., darkened, faded, and the like). In this example, seated position control 408, stand assist control 410, and bed flat and level control 412 in proning mode are non-selectable, such that pressing any of these icons during proning mode will result in the medical bed not carrying out such selected movements. For example, a user or the subject selecting the stand assist control 410 during proning mode will result in the no action in this embodiment, as moving the head portion of the medical bed upward for stand assist could cause pain and/or injury to the subject in the prone position. In some embodiments, an attempt to utilize a function not available during prone mode may results in a beep, tone, or a voice (digitally recorded or computer generated stating "function not available" for example).

By contrast, while in proning mode, other movement commands remain executable, and thus the icons remain selectable. The selectable icons in this embodiment include, by way of non-limiting example, bed exit alert status indicator 402 (i.e., to allow the user to select an alert if the subject tries to exit the medical bed), proning mode 404 (i.e., controlling whether to remain in proning mode), angle limit control 406 (i.e., limiting the angle that the subject can be at), bed length adjustment control 414 (i.e., modifying the position of the headboard and/or footboard), and scale menu control 416 (i.e., weighing the subject when the head support is not being utilized). In this example, these options do not pose a pain/injury risk to the subject in the prone position, and thus remain usable during proning mode.

Although a touch screen with a graphical user interface 400 is depicted in this embodiment, any interface screen may receive input via a control panel, such as a user control panel (FIGS. 1B and 2B) and/or a subject control panel (FIGS. 1C and 2C), by way of non-limiting example. In some embodiments, a graphical user interface 400 may be displayed on a device external to the medical bed, such as a separate monitor in the room. Any medical bed functionalities discussed with respect to the user control panel and/or subject control panel may be implemented in a graphical user interface 400. The graphical user interface 400 may be presented on a touch-screen or any other suitable display.

Figure 5:
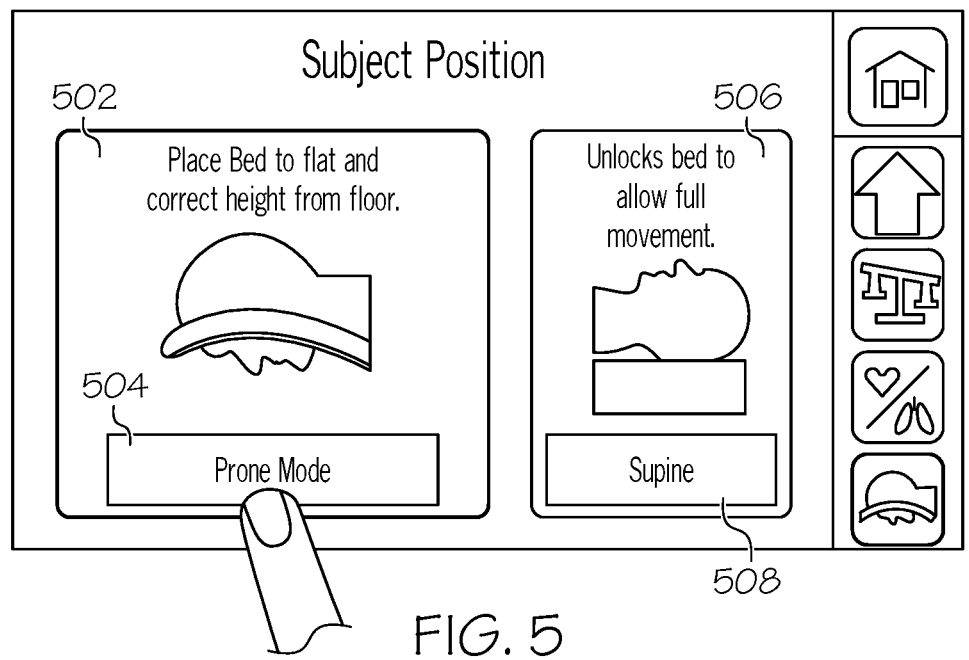
FIG. 5 depicts an exemplary mode selection graphical user interface, according to one or more embodiments shown and described herein.

FIG. 5 depicts an exemplary mode selection graphical user interface 500. The user may be provide prone mode directions 502 and/or supine mode directions 506, along with a respective prone mode confirmation 504 and/or a supine mode confirmation 508. In other embodiments, the prone mode confirmation 504 and/or a supine mode confirmation 508 may not be displayed unless the user first selects prone mode directions 502 and/or supine mode directions 506. If the prone mode confirmation 504 is selected, then various options may be restricted, as illustrated further with respect to FIGS. 6-8 and 10-14. Otherwise, if the supine mode confirmation 508 is selected, then the full functionality of the medical bed may be available. This is illustrated further with respect to FIG. 9.

Figure 6:
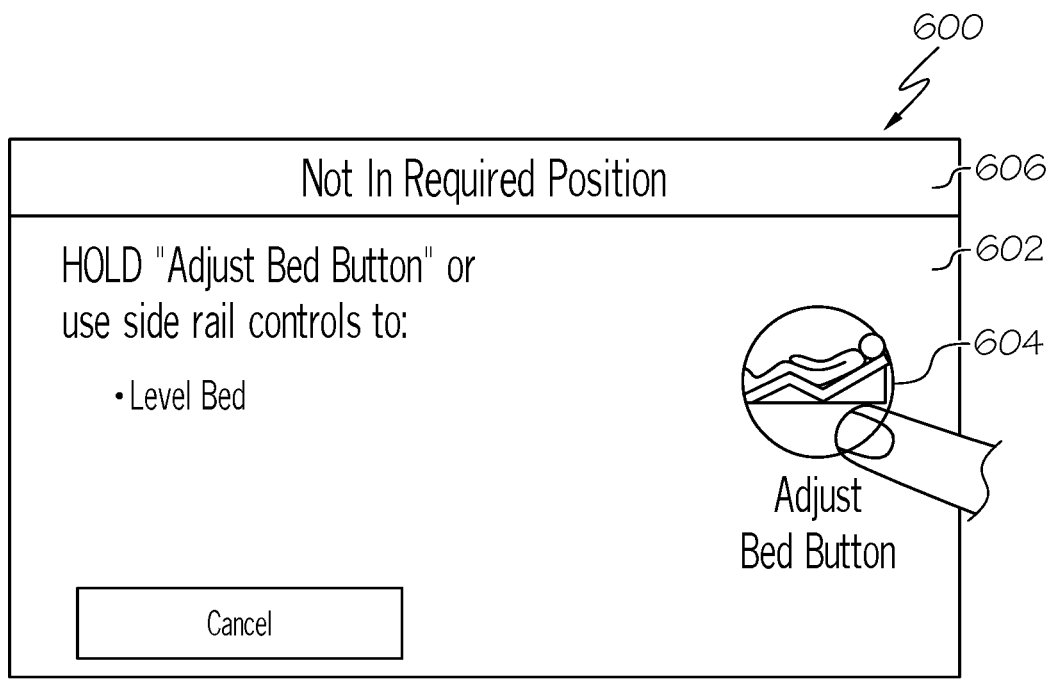
FIG. 6 depicts an exemplary restricted movement notification within a proning mode compliance interface 600, according to one or more embodiments shown and described herein.
Figure 8:
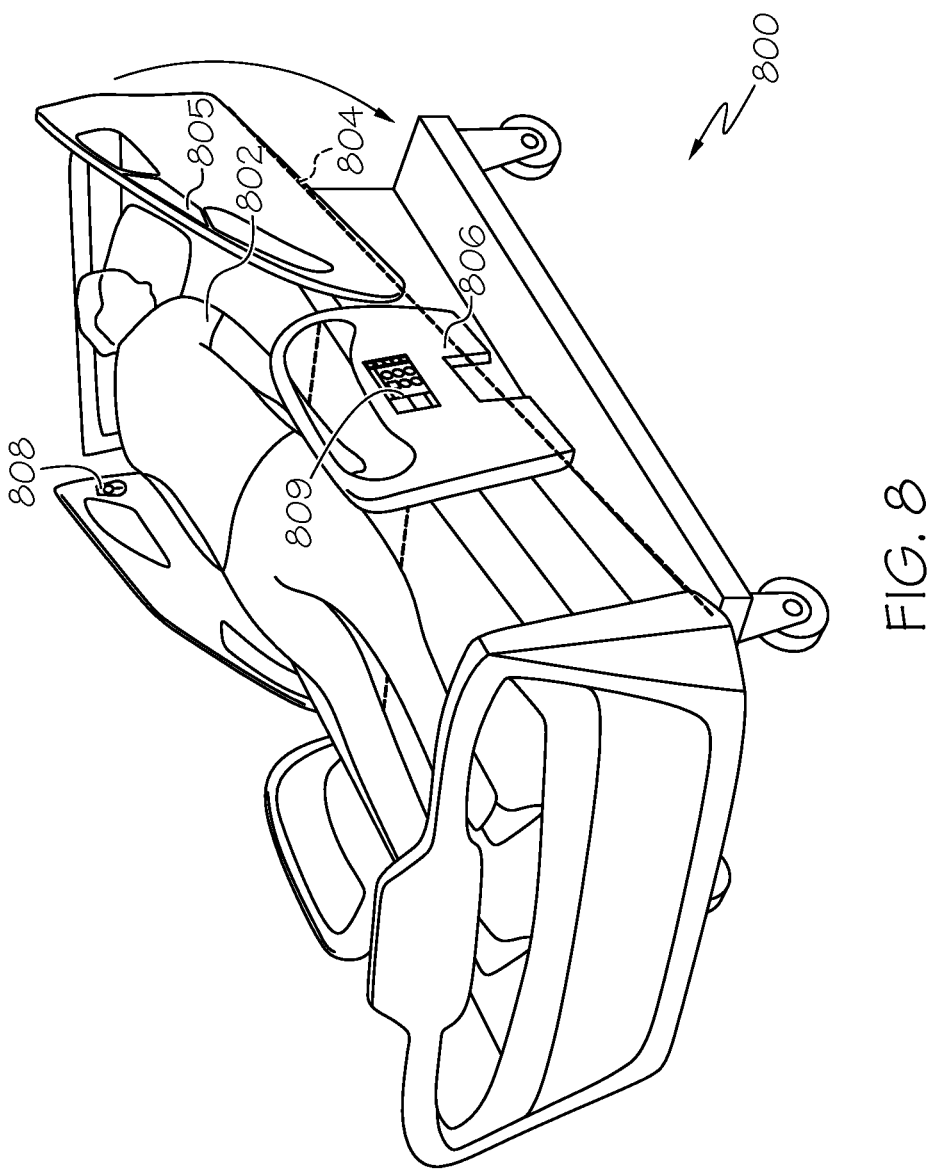
FIG. 8 depicts the medical bed of FIG. 1A containing a person in a prone position and articulating to come into position to enter proning mode, according to one or more embodiments shown and described herein.

FIG. 6 depicts an exemplary restricted movement notification within a proning mode compliance interface 600. In some embodiments, criteria may need to be satisfied before the medical bed can be placed into proning mode. In this embodiment, the list of required positions (i.e., criteria) may include the medical bed being level, such as ensuring that the legs of the subject are straight, lowering the back of the subject, and the out-of-bed exit mode being activated (i.e., utilizing the head support depicted in FIGS. 3A and 3B). For example, FIG. 8 depicts the subject in the prone position on a medical bed. Given that the subject's back needs to be lowered and the medical bed is not sufficiently level, due to the head portion of the medical bed being elevated, the required position states that the user should press the bed adjustment button 604 to level the medical bed. In some embodiments, the bed adjustment button 604 may be used to move one aspect of the medical bed at a time to bring it into compliance with the proning mode requirements. In other embodiments, the bed adjustment button 604 may be utilized to move the bed to address all proning mode requirements together. For example, pressing the bed adjustment button 604 may lower the medical bed and at the same time also lower the foot portion of the medical bed to conform to a destination state of being in prone mode (i.e., having the head portion, middle portion, and foot portion being substantially and horizontally level with respect to each other). For example, if the foot portion is tilted lower than the middle portion (being substantially horizontal in this example), the foot portion would be rotated to become substantially level with the middle portion. Similarly, if the head portion is at a higher tilt than the middle portion, the head portion would be lowered until it is substantially level with the middle portion.

Figure 7:
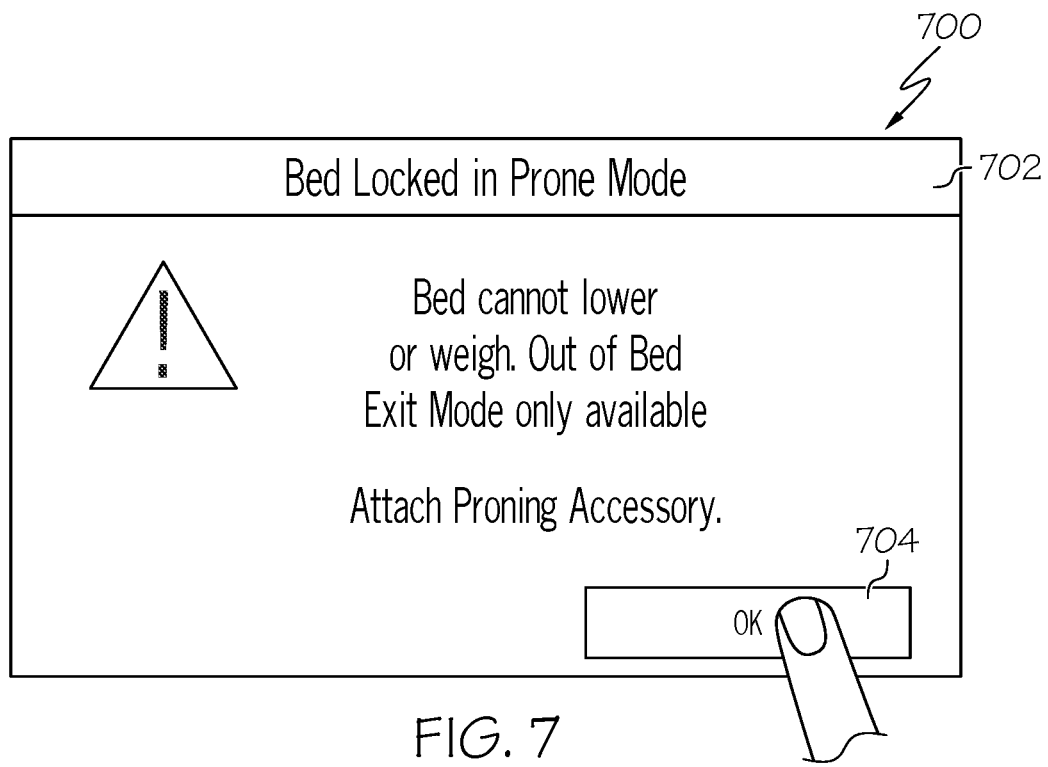
FIG. 7 depicts an exemplary prone mode lock indicator within a proning mode lock interface, according to one or more embodiments shown and described herein.

FIG. 7 depicts an exemplary prone mode lock indicator 704 within a proning mode lock interface 700. Continuing with the example of FIG. 6, all the conditions for proning mode have now been met (e.g., having a level bed, straightened subject legs, lower subject back section, and out of bed exit mode being on). Non-limiting examples of locked-out (or restricted) functions in proning mode may include, by way of non-limiting example, position bed mode, exit bed mode, back movement, leg movement, Trendelenburg position, reverse Trendelenburg position, chair position, boost, bed up/down, and the like. A prone mode lock notification 702 may be displayed, which may be part of a color notification scheme. For example, the prone mode lock notification 702 may be of a color that corresponds to display lights indicating proning mode for consistency across the medical bed. In this embodiment, an audio alert such as a beep, tone, or a voice (digitally recorded or computer generated) may also indicate that proning mode has been entered. Here, the user may have tried to select, for example, an option to weigh the subject (such as the scale menu control 416 in the graphical user interface of FIG. 4 or the bed up/down controls with lockout indicator 156 in the user control panel of FIG. 1B). In this embodiment, only the out of bed exit mode (i.e., exiting the mode utilizing the head support attachment) is available at this point due to being in proning mode. A prompt for attaching the proning accessory (such as the head support depicted in FIGS. 3A and 3B) may be provided.

FIG. 8 depicts the medical bed of FIG. 1A containing a person in a prone position and articulating to come into proper position to enter proning mode. Here, the medical bed 800 has the subject 802 in reverse Trendelenburg position. The downward arcing arrow indicates that the head portion of the medical bed 800 is lowering to straighten out the subject's 802 back. In this embodiment, the bed adjustment button discussed in FIG. 6 may be a touch-screen button on the graphical user interface 809 located on the lower side rail 806 or a physical button, such as on the control panel 805 or the subject controls 808 on the upper side rail 804. In one embodiment, the Trendelenburg control 234 button may be utilized to level the medical bed frame for proning mode, which could be used bring the medical bed 800 into compliance if the head support 300A is not attached, whereas the Trendelenburg control 234 button would not suffice for bringing the medical bed 800 into compliance if the head support 300A is attached, given that the subject's head would not be level with receiving portion 216 of the medical bed 800.

Figure 9:
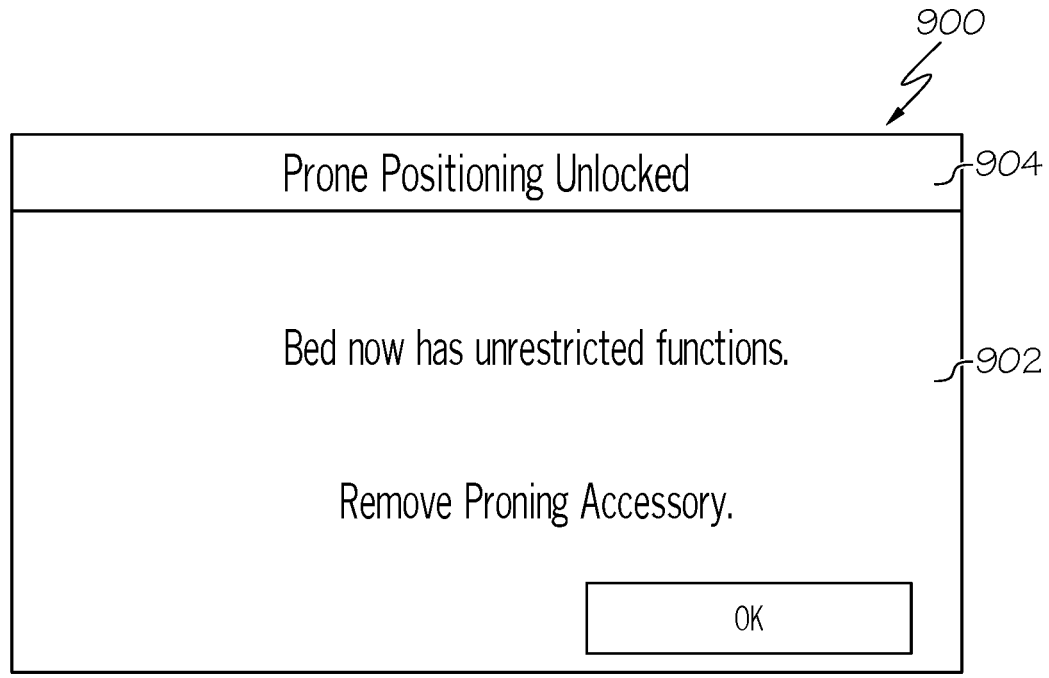
FIG. 9 depicts an exemplary prone positioning unlocking within a graphical user interface, according to one or more embodiments shown and described herein.

FIG. 9 depicts prone positioning unlocking within a graphical user interface 900. This may correspond, for example, to selection of supine mode as discussed with respect FIG. 5. This may include an unlocked prone positing notification 902. For example, if a proning accessory such as the head support depicted in FIGS. 3A and 3B is attached, the user may be prompted to remove it. The interface may also provide an unlocked prone positing indicator 904, which may include an on-screen notification, a light (such as an indicator light on the medical bed), an audio alert (such as a beep), and the like.

Figure 10:
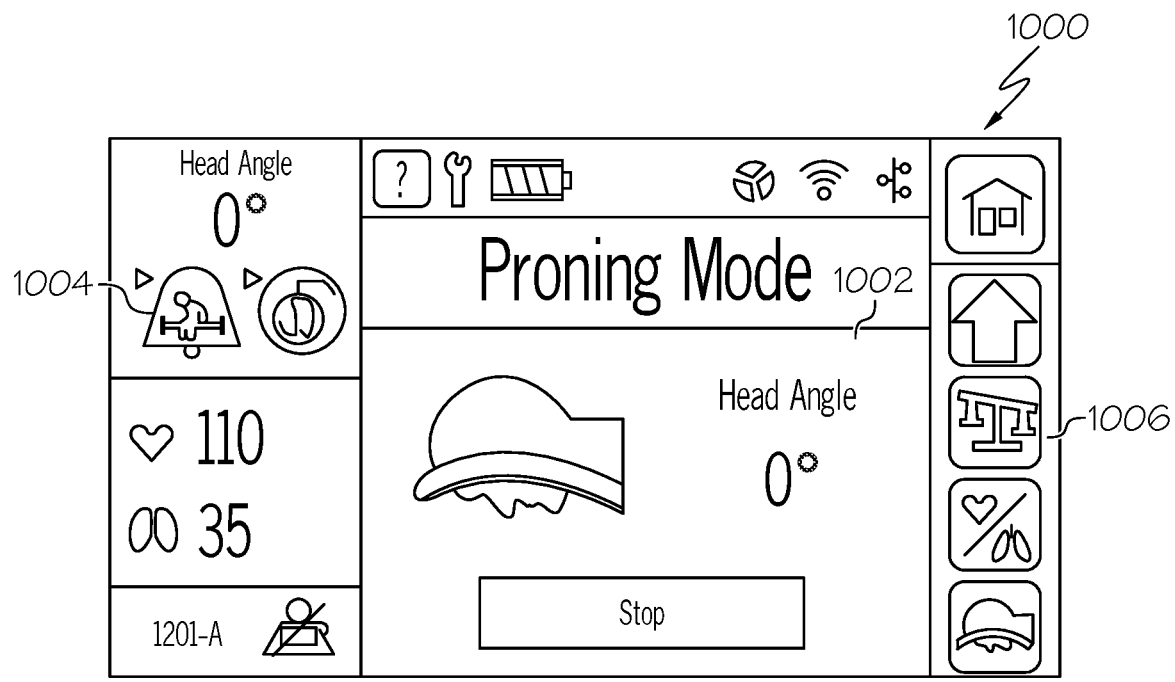
FIG. 10 depicts an exemplary proning mode graphical user interface, according to one or more embodiments shown and described herein.

FIG. 10 depicts an exemplary proning mode graphical user interface 1000. An interface depicting the active proning mode 1002 may be displayed with information such as whether a head support device is employed and the angle of the user's head while prone. While some functionality may not be available, other functionality such as the bed exit alert ON indicator 1004 and/or scale mode control 1006 utilized to weigh the user, may be utilized while in proning mode.

Figure 11:
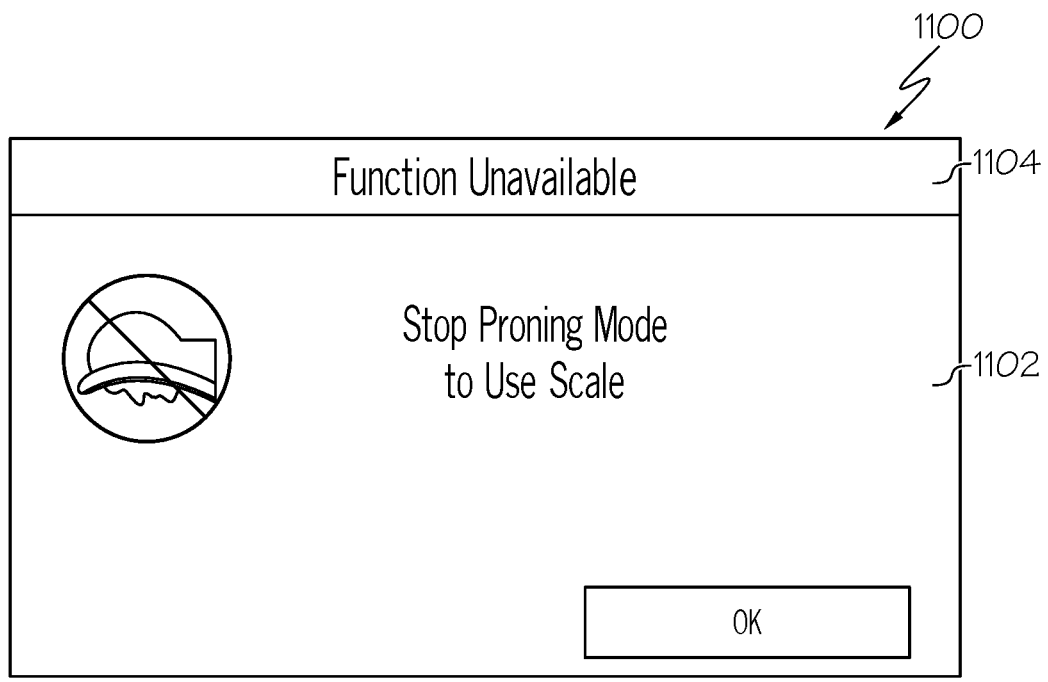
FIG. 11 depicts an exemplary graphical user interface depicting function unavailability during proning mode, according to one or more embodiments shown and described herein.

FIG. 11 depicts an exemplary proning mode restriction graphical user interface 1100 showing the unavailability of functionality during proning mode, such as scale mode as depicted here to weigh the user in the medical bed. This may be implemented to prevent, for example, the weighing of the user when their head is off of the medical bed and is instead supported by the head support. Otherwise, the lack of weight of the head could produce an inaccurate value. A proning mode restriction notification 1102 may be provided to notify the user of this restriction. A proning mode restriction indicator 1104 may be output via an on-screen notification (shown here), a light (such as an indicator light on the medical bed), an audio alert (such as a beep), and the like.

Figure 12:
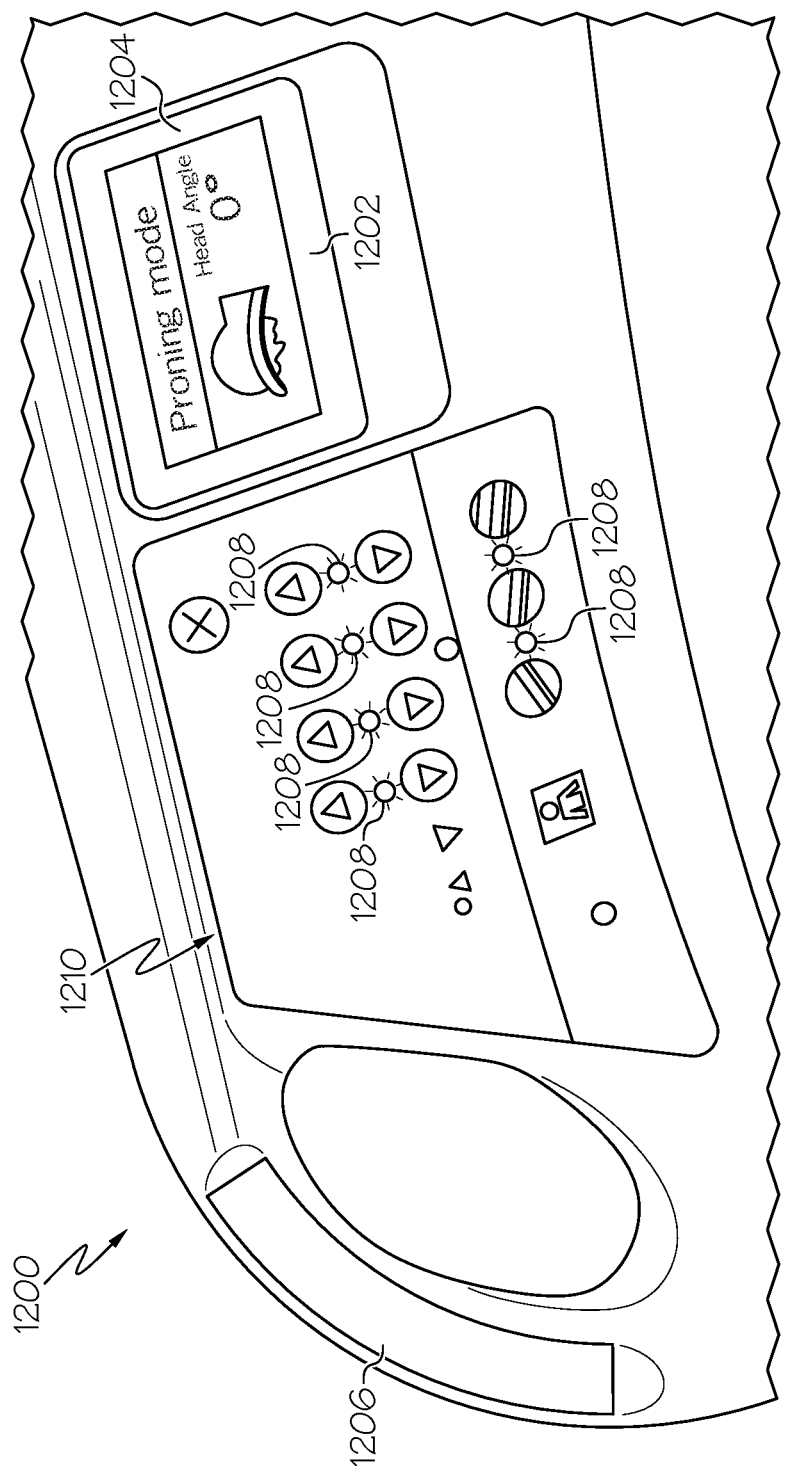
FIG. 12 depicts an exemplary control panel that may be utilized by medical personnel to move a medical bed with control options marked as restricted by indicator lights, according to one or more embodiments shown and described herein.

FIG. 12 depicts a panel 1200 with a graphical user interface 1202 on a touch screen 1204 and a user control panel 1210 that may be utilized by a user to move a medical bed, and may be located on any suitable portion of the medical bed, such as the lower side rail 106 depicted in FIG. 1A. In this embodiment, proning mode may be detected by movement of the actuators in the medical bed. The actuators may report the actuated states of, for example, the head portion 120, middle portion 122, and foot portion 124 of the medical bed 100A depicted in FIG. 1A. The processor may determine from the data communicated by the actuators under the foot portion 124 that it is in a horizontal position, whereas the actuators under the middle portion 122 report that it is also substantially horizontal, such that the processor determines that both portions are substantially horizontal and level with each other. Similarly, actuators under the head portion report that it is substantially horizontal, such that the processor also determines that the head portion 120 is substantially level with the middle portion 122, and that each portion is substantially horizontal relative to each other. Thus, in this embodiment, these prerequisites for proning mode, along with the out-of-bed exit mode discussed herein with respect to FIGS. 13-14, may result in the notifications of proning mode, such as a proning mode color indicator 1206 on the panel 1200 (or, in other embodiments, anywhere suitable on the medical bed or located remotely therefrom) allows the user to note at-a-glance that the medical bed is in proning mode. The proning mode color indicator 1206 may correspond to the proning mode color indicator 113 depicted in FIG. 1. Additionally, proning mode may also be indicated in this embodiment on the graphical user interface 1202, which may correspond to the graphical user interface 109 displayed on the lower side rail 106 of the medical bed 100A in FIG. 1A.

Figure 16:
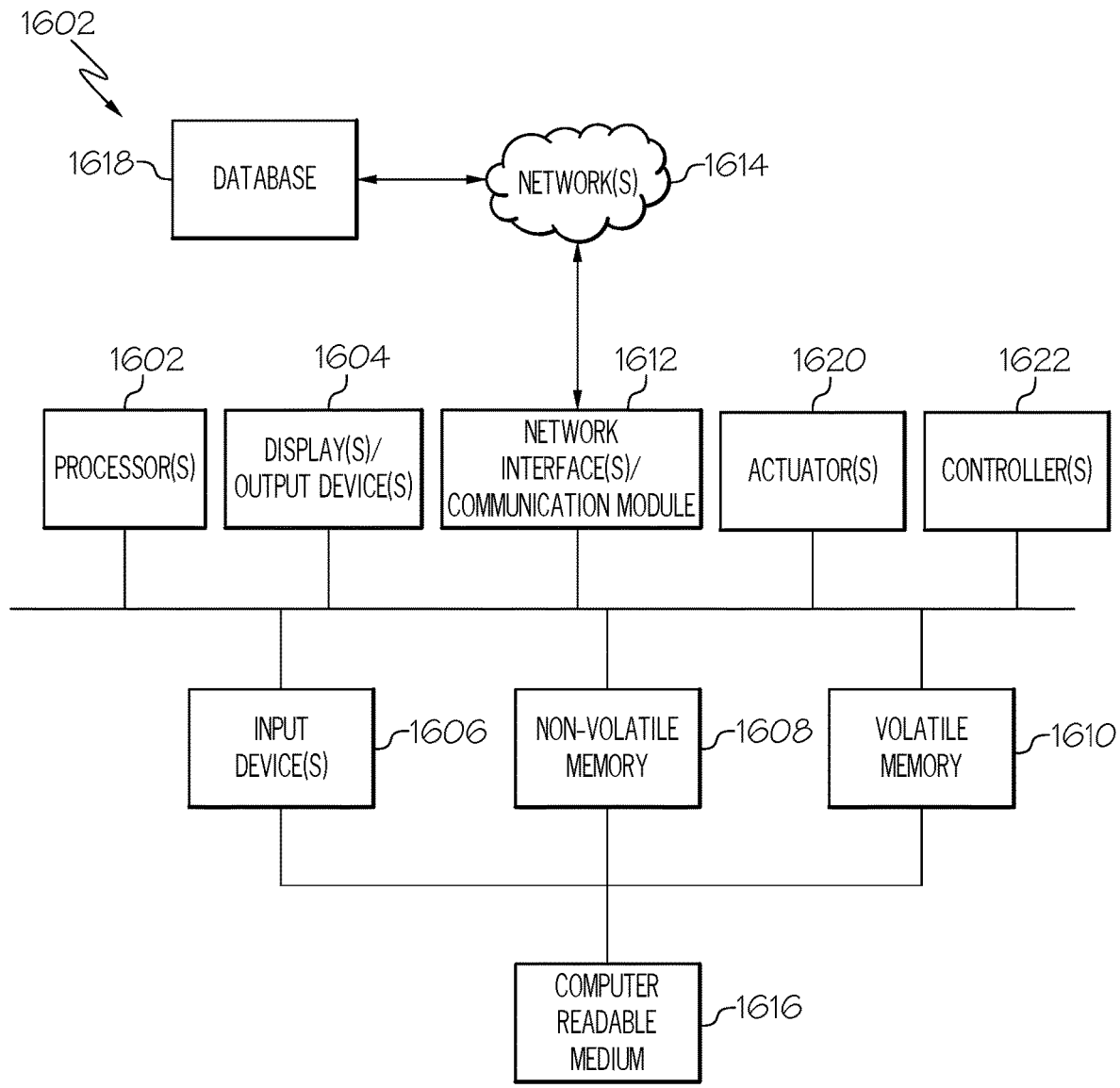
FIG. 16 depicts illustrative computing hardware that may be utilized to implement the various embodiments of a medical bed and associated methods herein, according to one or more embodiments shown and described herein.

In other embodiments, proning mode may be predicated upon the weight of a subject being detected by the weight sensors and reported to the processor (depicted as 1602 in FIG. 16). The processor could then send instructions to the graphical user interface 1202 and/or user control panel 1210 to indicate proning mode is active. Control options, here depicted as buttons, have associated proning mode lighting indicator lights 1208 that denote whether the movement associated with the button(s) is restricted due to proning mode. In other embodiments, the indicator lights may blink and/or use colors to indicate different modes of operation (such as one color to represent proning mode, another to color to represent regular operation).

Figure 13:
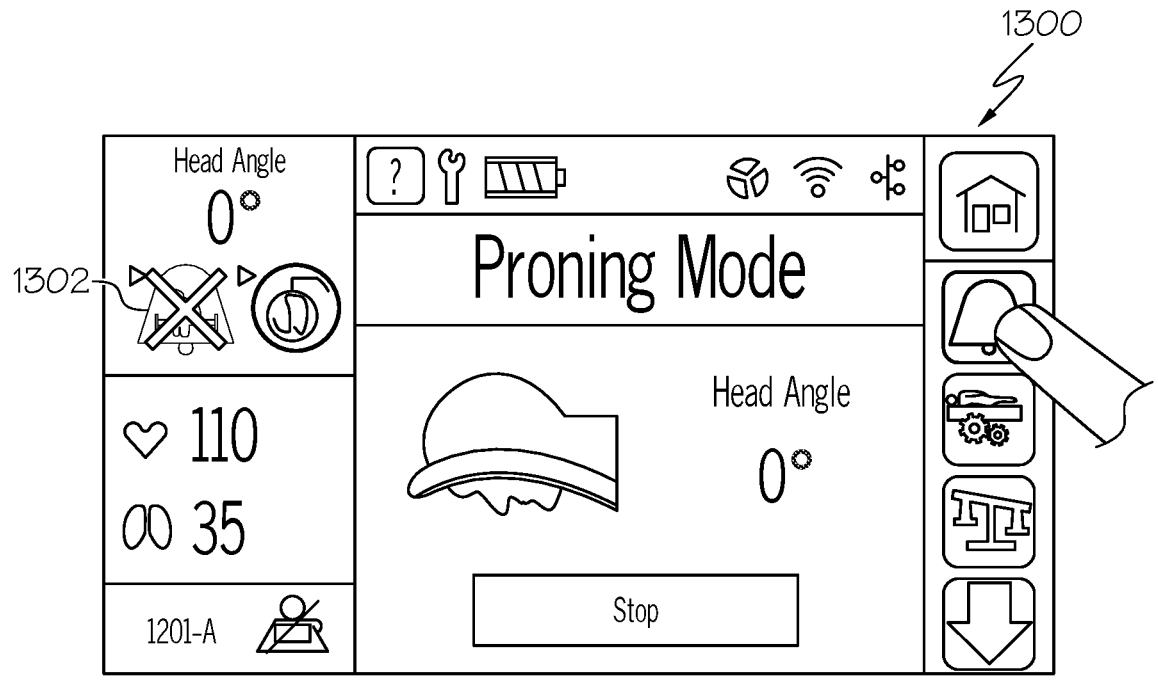
FIG. 13 depicts an exemplary proning mode alert interface, according to one or more embodiments shown and described herein.

FIG. 13 depicts an exemplary proning mode alert interface 1300 while in proning mode. In this embodiment, the bed exit alert 1302 (or out-of-bed exit alert) is displayed, as a prerequisite for proning mode. For example, if a subject is left alone in prone position in the medical bed, it may be beneficial to alert the user that the subject is trying to get out of the medical bed. For example, weight sensors 126 depicted in FIG. 1A may be utilized to communicate to a processor (depicted as 1602 in FIG. 16) detect movement of the subject upon the support surface 112 within the medical bed and/or if the subject attempts to leave the medical bed. In turn, upon detection of such movement(s) by the weight sensors, the processor may send an alert to a display or other output device (such as a speaker), in which the alert may be audio (such as a beep, tone, voice, and the like) or visual (blinking light, and the like). In an additional example, the use of a head support 300 as depicted in FIGS. 3A and 3B may be detected by the socket sensors 317 located in the sockets 318 upon which the attachment members 316 of the head support 300 push down. The socket sensors 317 may report the detected weight to the processor (depicted for example as 1602 in FIG. 16), which may in turn report this data head support data to the proning mode alert interface 1300 to display notification regarding use of the head support 300.

Figure 14:
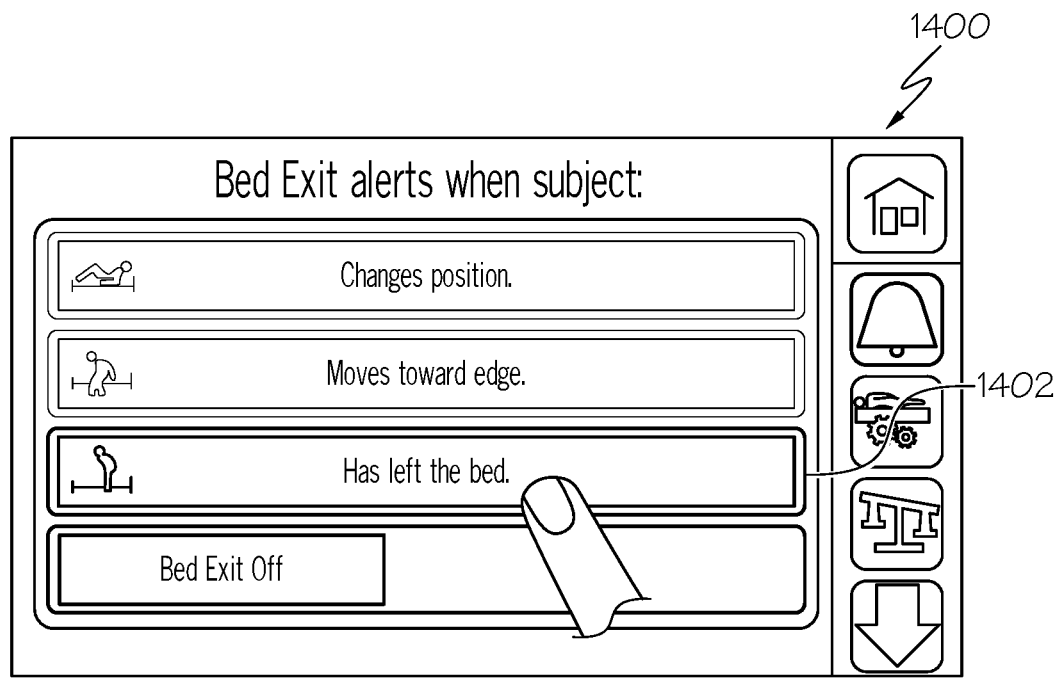
FIG. 14 depicts an exemplary bed exit alert interface, according to one or more embodiments shown and described herein.

FIG. 14 depicts an exemplary bed exit alert interface. In some embodiments, some options may be visually displayed as unavailable (in prone mode, for example) utilizing any suitable indicator, such as fading or darkening any bed exit alert options not selected. As discussed with respect to FIG. 13, a user may want to know what the subject is doing in the medical bed, particularly if unable to directly observe the subject. The selected bed exit alert option 1402 may be used (such as during proning mode) to determine whether the subject has left the medical bed, although other selectable options may include whether the subject changes their position or moves towards the edge of the medical bed. For example, a user setting bed alerts on the bed exit alert interface 1400, which may be located on the lower side rail 106 of the medical bed 100A depicted in FIG. 1A, such that the instructions are received at the processor (depicted for example as 1602 in FIG. 16), which can utilize incoming data from the weight sensors 126 depicted in FIG. 1A to determine whether an alert is warranted based upon whether the weight sensors 126 detect that the subject has changed their position atop the support surface 112, moved towards the edge of the medical bed (such as the head rail 108, lower side rail 106, foot rail 100, etc.), and/or has left the medical bed entirely. In turn, upon detection of such movement(s) by the weight sensors, the processor may send an alert to a display or other output device (such as a speaker), in which the alert may be audio (such as a beep, tone, voice, and the like) or visual (blinking light, and the like).

Figure 15:
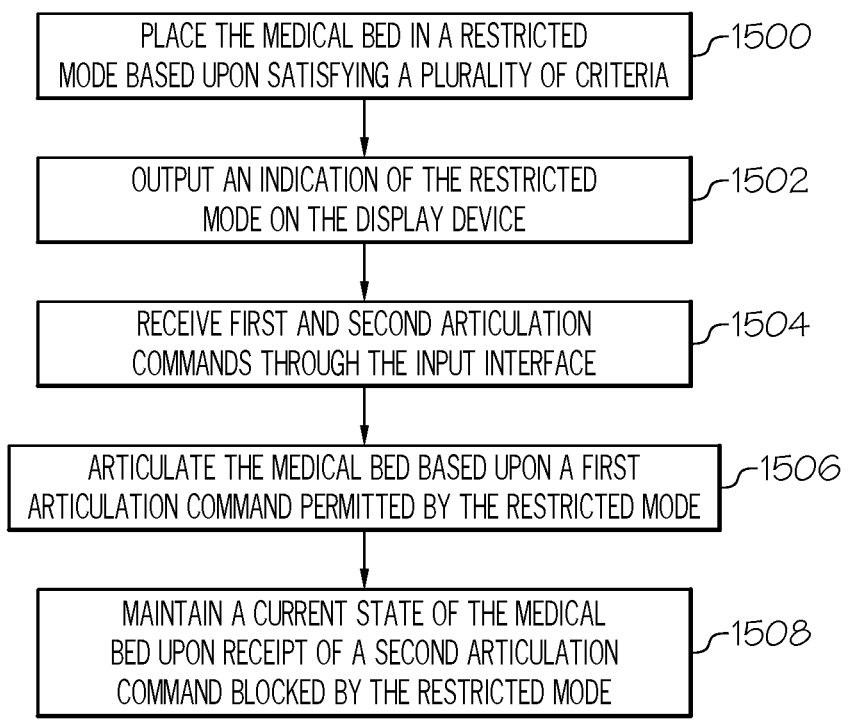
FIG. 15 depicts an exemplary flowchart for conditionally-restricted medical bed operation, according to one or more embodiments shown and described herein.

FIG. 15 depicts an exemplary flowchart for conditionally-restricted medical bed operation. At block 1500, the medical bed is placed in a restricted mode based upon satisfying a plurality of criteria. As discussed herein, criteria may include the medical bed being level, the medical bed being configured to straighten legs of a subject in the medical bed, the medical bed being configured to lower a back of the subject in the medical bed, and/or an out-of-bed exit mode being on. At block 1502, the display device outputs an indication of the restricted mode. For example, the prone mode lock notification may be of a color that corresponds to display lights indicating proning mode for consistency across the medical bed, and/or an audio alert such as a beep, tone, or a voice (digitally recorded or computer generated) may also indicate that proning mode has been entered. At block 1504, the input interface receives first and second movement commands. For example, a first command may be for the bed length adjustment control (i.e., modifying the position of the headboard and/or footboard), while the second command may be for stand assist control. At block 1506, the medical bed is moved based upon a first movement command as permitted by the restricted mode. Here, the bed length adjustment control does not interfere with the proning mode operation (i.e., does not materially change the patient's prone position). At block 1508, a current state of the medical bed is maintained upon receipt of a second movement command that is blocked by the restricted mode. Continuing with this example, the stand-assist command is not executed, because it would raise the subject's torso and head, interfering with the prone position.

FIG. 16 depicts illustrative computing hardware that may be utilized to implement the various embodiments of a medical bed 1600, which as described herein is but one example of a suitable computing device and does not suggest any limitation on the scope of any embodiments presented. The medical bed 1600 in some embodiments may also be utilized to implement the medical beds depicted in FIGS. 1A, 2A, and 8 (including via a processor 1602), the control panels depicted in FIGS. 1B, 1C, 2B, 2C, and 12 (such as via the input devices 1606), the graphical user interfaces (such as via the displays/output devices 1604) depicted in FIGS. 4-7, 9-11, and 13-14, and/or any combination thereof. Nothing illustrated or described with respect to the medical bed 1600 should be interpreted as being required or as creating any type of dependency with respect to any element or plurality of elements. In an embodiment, the medical bed 1600 includes at least one processor 1602 and memory comprising non-volatile memory 1608 and/or volatile memory 1610. The medical bed 1600 can include one or more displays and/or output devices 1604 such as, for example, monitors, speakers, headphones, projectors, wearable-displays, holographic displays, and/or printers. For example, the proning mode lighting indicator light 1208 and/or proning mode color indicator 1206 depicted in FIG. 12 may include a light emitting diode, indicator light, and/or the like.

The medical bed 1600 may further include one or more input devices 1606 which can include, by way of example, any type of mouse, keyboard, disk/media drive, memory stick/thumb-drive, memory card, pen, touch-input device, biometric scanner, voice/auditory input device, motion-detector, camera, scale, and any device capable of measuring data such as motion data (e.g., an accelerometer, GPS, a magnetometer, a gyroscope, etc.), biometric data (e.g., blood pressure, pulse, heart rate, perspiration, temperature, voice, facial-recognition, motion/gesture tracking, gaze tracking, iris or other types of eye recognition, hand geometry, oxygen saturation, glucose level, fingerprint, DNA, dental records, weight, or any other suitable type of biometric data, etc.), video/still images, and audio (including human-audible and human-inaudible ultrasonic sound waves). Input devices 1606 may include user control panels and/or subject control panels (membrane switch panels, and the like), sensors (weight sensors, proximity sensors, and the like), and/or cameras (with or without audio recording), and/or cameras (digital and/or analog cameras, still cameras, video cameras, thermal imaging cameras, infrared cameras, cameras with a charge-couple display, night-vision cameras, three-dimensional cameras, webcams, audio recorders, and the like).

The medical bed 1600 typically includes non-volatile memory 1608 (e.g., ROM, flash memory, etc.), volatile memory 1610 (e.g., RAM, etc.), or a combination thereof. A network interface 1612 can facilitate communications over a network 1614 with other data source such as a database 1618 via wires, a wide area network, a local area network, a personal area network, a cellular network, a satellite network, and the like, regarding any suitable type of data such as the current proning mode status of a medical bed that is being reported a remote device such as a server, by way of non-limiting example. Suitable local area networks may include wired Ethernet and/or wireless technologies such as, for example, wireless fidelity (Wi-Fi). Suitable personal area networks may include wireless technologies such as, for example, IrDA, Bluetooth, Wireless USB, Z-Wave, ZigBee, and/or other near field communication protocols. Suitable personal area networks may similarly include wired computer buses such as, for example, USB and FireWire. Suitable cellular networks may include, but are not limited to, technologies such as LTE, WiMAX, UMTS, CDMA, and GSM. Network interface 1612 can be communicatively coupled to any device capable of transmitting and/or receiving data via one or more network(s) 1614. Accordingly, the network interface 1612 can include a communication transceiver for sending and/or receiving any wired or wireless communication. For example, the network interface 1612 may include an antenna, a modem, LAN port, Wi-Fi card, WiMax card, mobile communications hardware, near-field communication hardware, satellite communication hardware and/or any wired or wireless hardware for communicating with other networks and/or devices. The network interface 1612 may include a transceiver configured to transmit and to receive wireless signals (e.g., RFID, RF, Bluetooth, UWB, and/or the like) according to the respective wireless protocols. In some aspects, data transmission techniques including encryption/decryption, forward error correction, and/or the like may be instituted. The location of the medical bed 1600 may be determined utilizing any suitable protocol include Global Positioning System (GPS), a Global Navigation Satellite System (GLONASS), a Wi-Fi locating system, cellular networks, radio frequency ID (RFID), and/or the like.

A computer-readable medium 1616 may include a plurality of computer readable mediums, each of which may be either a computer readable storage medium or a computer readable signal medium. A computer readable storage medium may reside, for example, within an input device 1606, non-volatile memory 1608, volatile memory 1610, or any combination thereof. A computer readable storage medium can include tangible media that is able to store instructions associated with, or used by, a device or system. A computer readable storage medium includes, by way of example: RAM, ROM, cache, fiber optics, EPROM/Flash memory, CD/DVD/BD-ROM, hard disk drives, solid-state storage, optical or magnetic storage devices, diskettes, electrical connections having a wire, or any combination thereof. A computer readable storage medium may also include, for example, a system or device that is of a magnetic, optical, semiconductor, or electronic type. Computer readable storage media and computer readable signal media are mutually exclusive.

A computer readable signal medium can include any type of computer readable medium that is not a computer readable storage medium and may include, for example, propagated signals taking any number of forms such as optical, electromagnetic, or a combination thereof. A computer readable signal medium may include propagated data signals containing computer readable code, for example, within a carrier wave. Computer readable storage media and computer readable signal media are mutually exclusive.

The medical bed 1600 may include one or more network interfaces 1612 to facilitate communication with one or more remote devices, which may include, for example, client and/or server devices. The network interface 1612 may also be described as a communications module, as these terms may be used interchangeably. The database 1618 is depicted as being accessible over the network 1614 and may reside within a server, the cloud, or any other configuration to support being able to remotely access data and store data in the database 1618, which may utilized any suitable data such as proning mode historical data and/or electronic medical records relating to the utilization of the medical bed 1600. The network interface 1612 may generally provide the medical bed 1600 with an ability to interface with one or more external devices, such as, for example, a medical facility server, a nurse station, and/or the like. Communication with external devices may occur using various communication ports (not shown). An illustrative communication port may be attached to a communications network, such as the Internet, an intranet, a local network, a direct connection, and/or the like.

The medical bed 1600 may include one or more actuators 1620 and controllers 1622 to facilitate communication with one or more remote devices. An actuator 1620 to move various portions of the medical bed 1600 may utilize, by way of non-limiting example, an electric motor or a pneumatic or hydraulic system a linear actuator, a precision actuator, a stepper motor, a direct current motor, a rodless actuator, a pneumatic actuator, an electromagnetic rail actuator, a rack and pinion actuator, a pulley actuator, a micro-positioning linear actuator, a nano-positioning linear actuator, a gear motor actuator, a segmented spindle actuator, or any other suitable type of actuator. A controller 1622 may include any suitable computing device capable of providing instructions to and/or receive feedback from an actuator 1620. A controller 1622 may be and/or include a microcontroller, remote controller, input device, switch, and the like.

It should be understood that the components illustrated in FIG. 16 are merely illustrative and are not intended to limit the scope of this disclosure. More specifically, while the at least some of the components in FIG. 16 are illustrated as residing within the medical bed 1600, this is a non-limiting example. In some embodiments, one or more of the components may reside external to the medical bed 1600. Similarly, one or more of the components may be embodied in other devices not specifically described herein.

It should now be understood that the systems and methods described herein are suitable for utilizing a proning mode to restrict movement of a medical bed in specific ways. In particular, the systems and methods described herein utilize multiple criteria to determine whether the medical bed is ready to enter the proning mode and provide an indication (visual, audio, etc.) on a graphical interface and/or control panel that certain functionality is not available, which may be based upon a user inputting a command or a general unavailability indicator. An input may be requested to confirm that proning mode is being requested. Such systems and methods ensure that the movement of the medical bed is restricted is certain ways to protect a user lying in a prone position.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A medical bed, comprising:
a processor;
an input interface configured to receive commands;

a display device configured to display an output;
a non-transitory memory storing program instructions, the program instructions, when executed by the processor, causing the processor to:
place the medical bed in a restricted mode based upon satisfying a plurality of criteria comprising at least one of:
the medical bed being level,
the medical bed being configured to straighten legs of a subject supported on the medical bed,
the medical bed being configured to lower a back of the subject in the medical bed, and
an out-of-bed exit mode being on;
output an indication of the restricted mode on the display device;
receive first and second movement commands through the input interface, wherein the first and second movement commands are configured to move the medical bed;
move the medical bed to enter a proning mode based upon the first movement command permitted by the restricted mode, the plurality of criteria being associated with the proning mode; and
maintain a current state of the medical bed in the proning mode upon receipt of the second movement command blocked by the restricted mode, wherein the second movement command differs from the first movement command.

2. The medical bed of claim 1, wherein the restricted mode is based upon prior input confirming entry into the restricted mode.

3. The medical bed of claim 1, wherein exit from the restricted mode is contingent upon receipt of input confirming exit from the restricted mode.

4. The medical bed of claim 1, further comprising a head support device configured to support the head of the subject in a prone position of the proning mode.

5. The medical bed of claim 1, further comprising a communication component that indicates a current proning mode status to a remote device.

6. The medical bed of claim 1, wherein the memory stores data regarding proning mode historical data of the medical bed.

7. The medical bed of claim 1, wherein the second movement command comprises position bed mode, exit bed mode, back movement, leg movement, Trendelenburg position, reverse Trendelenburg position, chair position, boost, or bed up/down.

8. The medical bed of claim 1, wherein the second movement command being blocked by the restricted mode results in a visual or audio notification.

9. The medical bed of claim 1, further comprising a bed adjustment input button configured to move the medical bed to satisfy all the criteria to enter the restricted mode.

10. The medical bed of claim 1, wherein the second movement command is blocked due to interference with the proning mode.

11. The medical bed of claim 1, wherein the first movement command remains executable during the proning mode and the second movement command is blocked during the proning mode.

12. A method for conditionally-restricted medical bed operation, the method comprising:
placing a medical bed in a restricted mode based upon satisfying a plurality of criteria comprising at least one of:
the medical bed being level,
the medical bed being configured to straighten legs of a subject supported on the medical bed,
the medical bed being configured to lower a back of the subject in the medical bed, and
an out-of-bed exit mode being on;
outputting an indication of the restricted mode on a display device of the medical bed;
receiving first and second movement commands through an input interface of the medical bed, wherein the first and second movement commands are configured to move the medical bed;
causing the medical bed to articulate to enter a proning mode based upon the first movement command permitted by the restricted mode, the plurality of criteria being associated with the proning mode; and
maintaining a current state of the medical bed in the proning mode upon receipt of the second movement command blocked by the restricted mode, wherein the second movement command differs from the first movement command.

13. The method of claim 12, wherein the restricted mode is based upon prior input confirming entry into the restricted mode.

14. The method of claim 12, wherein exit from the restricted mode is contingent upon receipt of input confirming exit from the restricted mode.

15. The method of claim 12, further comprising using a head support device to support the head of the subject in a prone position of the proning mode.

16. The method of claim 12, further comprising indicating a current proning mode status to a remote device via a communication component.

17. The method of claim 12, further comprising storing data regarding proning mode historical data of the medical bed.

18. The method of claim 12, wherein the second movement command comprises position bed mode, exit bed mode, back movement, leg movement, Trendelenburg position, reverse Trendelenburg position, chair position, boost, or bed up/down.

19. The method of claim 12, further comprising articulating the medical bed to satisfy all the criteria to enter the restricted mode based upon input received at a bed adjustment input button.

20. A system comprising:
a processor; and
a non-transitory, computer readable storage medium communicatively coupled to the processor, the non-transitory, computer readable storage medium comprising one or more programming instructions stored thereon that, when executed by the processor, cause the processor to:
place a medical bed in a restricted mode based upon satisfying a plurality of criteria comprising at least one of:
the medical bed being level,
the medical bed being configured to straighten legs of a subject supported on the medical bed,
the medical bed being configured to lower a back of the subject in the medical bed, and
an out-of-bed exit mode being on,
output an indication of the restricted mode on a display device of the medical bed,
receive first and second movement commands through an input interface of the medical bed, wherein the movement commands are configured to move the medical bed, cause the medical bed to articulate to enter a proning mode based upon the first movement command permitted by the restricted mode, the plurality of criteria being associated with the proning mode, and maintain a current state of the medical bed in the proning mode upon receipt of the second movement command blocked by the restricted mode, wherein the second movement command differs from the first movement command.

* * * * *